United States Patent [19]

Stoyanov et al.

[11] Patent Number: 5,885,777
[45] Date of Patent: Mar. 23, 1999

[54] CLONING, EXPRESSION AND CHARACTERIZATION OF A NOVEL FORM OF PHOSPHATIDYLINOSITOL-3-KINASE

[75] Inventors: Borislav Stoyanov, Dorndorf; Theodor Hanck, Jena; Reinhard Wetzker, Jena-Lobeda, all of Germany

[73] Assignee: Max-Planck-Gesellschaft Zur Forderung Der Wissenschaften E.V., Munich, Germany

[21] Appl. No.: 817,090

[22] PCT Filed: Oct. 10, 1995

[86] PCT No.: PCT/EP95/03990

§ 371 Date: Apr. 11, 1997

§ 102(e) Date: Apr. 11, 1997

[87] PCT Pub. No.: WO96/12024

PCT Pub. Date: Apr. 25, 1996

[30] Foreign Application Priority Data

Oct. 13, 1994 [DE] Germany .......................... 44 36 696.5
Dec. 20, 1994 [DE] Germany .......................... 44 45 562.3

[51] Int. Cl.⁶ .............................. C12Q 1/68; C07H 21/00; C12N 15/12; C12N 15/63
[52] U.S. Cl. ........................... 435/6; 435/320.1; 435/325; 435/252.3; 435/254.11; 435/254; 536/23.1; 536/23.2; 536/23.5; 536/24.3; 536/24.31
[58] Field of Search ......................... 435/6, 320.1, 172.3, 435/325, 252.3, 254.11, 254.2; 514/44, 23.2; 536/23.1, 23.5, 24.5, 24.31, 24.3

[56] References Cited

PUBLICATIONS

James, "Toward gene–inhibition therapy: a review of progress and prospects in the field of antiviral antisense nucleic acids and ribozymes", Antiviral Chemistry & Chemotherapy 2(4): 191–214, 1991.

Orkin et al., "Report and recommendations of the panel to assess the NIH investment in research on gene therapy", issued by the U.S. National Insitutes of Health, Dec. 1995.

Gura, "Antisense has growing pains", Science 270:575–577, Oct. 1995.

Science, Aug. 4, 1995, 269 (5224) P690–3, Stoyanov et al., Cloning and characterization of a G protein–activated human phosphoinositide–3 kinase.

Molecular and Cellular Biology, vol. 13, No. 12, Dec. 1993 pp. 7677–7688, Hu et al, Cloning of a novel, ubiquitously expressed human phosphatidylinositol 3–kinase and . . .

*Primary Examiner*—Jasemine C. Chambers
*Assistant Examiner*—Scott D. Priebe
*Attorney, Agent, or Firm*—Nikaido, Marmelstein, Murray & Oram, LLP

[57] ABSTRACT

The present invention concerns a new phosphatidyl-inositol-3-kinase (PI3Kγ), a nucleic acid coding for it, an antibody directed against the protein as well as the diagnostic and therapeutic use of the protein, the nucleic acid and the antibody.

11 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 4134 base pairs
        ( B ) TYPE: nucleic acid
        ( C ) STRANDEDNESS: both
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION:423..3569

( x i ) SEQUENCE DESCRIPTION: SEQ ID NO: 1:

```
GAATTCGGCA  CGAGCACTTC  CTTCTCGGCT  AGATTATCTG  AAACTGTTGT  CGGTTCTTGA      60

GATGATACTA  CCACCGAATG  TCTGTGTTTC  ATTGTCTAGT  CCAACCTGTA  TTGTGGATAT     120

CTACAACGTT  CCGGCAATAG  TTTTGCAGGT  GCATCACATT  TTTGTTTTTG  TTTTGGGAGG     180

AAAAGGGAGG  GCACGGCAGC  CAGGCTTCAT  ATTCCTACAA  GTGCATGCTT  CAAGATTACT     240

GTACTTACAG  TGTTTCCAAC  ATCTTCTCAT  AAAAGGGGAA  AGCTTCATAG  CCTCAACCAT     300
```

```
GAAGGAAACC AGTCGCATAG GGCATGGAGC TGGAGAACTA TAAACAGCCC GTGGTGCTGA        360

GAGAGGACAA CTGCCGAAGG CGCCGGAGGA TGAAGCCGCG CAGTGCTGCC AGCCTGTCCT        420

CC ATG GAG CTC ATC CCC ATC GAG TTC GTG CTG CCC ACC AGC CAG CGC          467
   Met Glu Leu Ile Pro Ile Glu Phe Val Leu Pro Thr Ser Gln Arg
        5                  10                  15

AAA TGC AAG AGC CCC GAA ACG GCG CTG CTG CAC GTG GCC GGC CAC GGC          515
Lys Cys Lys Ser Pro Glu Thr Ala Leu Leu His Val Ala Gly His Gly
             20                  25                  30

AAC GTG GAG CAG ATG AAG GCC CAG GTG TGG CTG CGA GCG CTG GAG ACC          563
Asn Val Glu Gln Met Lys Ala Gln Val Trp Leu Arg Ala Leu Glu Thr
                 35                  40                  45

AGC TGG CGC GGA CTT CTA CCA CCG GCT GGG ACC GCA TCA CTT CCT CCT          611
Ser Trp Arg Gly Leu Leu Pro Pro Ala Gly Thr Ala Ser Leu Pro Pro
             50                  55                  60

GCT CTA TCA GAA GAA GGG CAG TGG TAC GAG ATC TAC GAC AAG TAC CAG          659
Ala Leu Ser Glu Glu Gly Gln Trp Tyr Glu Ile Tyr Asp Lys Tyr Gln
         65                  70                  75

GTG GTG CAG ACT CTG GAC TGC CTG CGC TAC TGG AAG GCC ACG CAC CGG          707
Val Val Gln Thr Leu Asp Cys Leu Arg Tyr Trp Lys Ala Thr His Arg
 80                  85                  90                  95

AGC CCG GGC CAG ATC CAC CTG GTG CAG CGG CAC CCG CCC TCC GAG GAG          755
Ser Pro Gly Gln Ile His Leu Val Gln Arg His Pro Pro Ser Glu Glu
                     100                 105                 110

TCC CAA GCC TTC CAG CGG CAG CTC ACG GCG CTG ATT GGC TAT GAC GTC          803
Ser Gln Ala Phe Gln Arg Gln Leu Thr Ala Leu Ile Gly Tyr Asp Val
                 115                 120                 125

ACT GAC GTC AGC AAC GTG CAC GAC GAT GAG CTG GAG TTC ACG CGC CGT          851
Thr Asp Val Ser Asn Val His Asp Asp Glu Leu Glu Phe Thr Arg Arg
             130                 135                 140

GGC TTG GTG ACC CCG CGC ATG GCG GAG GTG GCC AGC CGC GAC CCC AAG          899
Gly Leu Val Thr Pro Arg Met Ala Glu Val Ala Ser Arg Asp Pro Lys
145                 150                 155

CTC TAC GCC ATG CAC CCG TGG GTG ACG TCC AAG CCC CTC CCG GAG TAC          947
Leu Tyr Ala Met His Pro Trp Val Thr Ser Lys Pro Leu Pro Glu Tyr
160                 165                 170                 175

CTG TGG AAG AAG ATT GCC AAC AAC TGC ATC TTC ATC GTC ATT CAC CGC          995
Leu Trp Lys Lys Ile Ala Asn Asn Cys Ile Phe Ile Val Ile His Arg
                 180                 185                 190

AGC ACC ACC AGC CAG ACC ATT AAG GTC TCA CCC GAC GAC ACC CCC GGC         1043
Ser Thr Thr Ser Gln Thr Ile Lys Val Ser Pro Asp Asp Thr Pro Gly
             195                 200                 205

GCC ATC CTG CAG AGC TTC TTC ACC AAG ATG GCC AAG AAG AAA TCT CTG         1091
Ala Ile Leu Gln Ser Phe Phe Thr Lys Met Ala Lys Lys Lys Ser Leu
         210                 215                 220

ATG GAT ATT CCC GAA AGC CAA AGC GAA CAG GAT TTT GTG CTG CGC GTC         1139
Met Asp Ile Pro Glu Ser Gln Ser Glu Gln Asp Phe Val Leu Arg Val
     225                 230                 235

TGT GGC CGG GAT GAG TAC CTG GTG GGC GAA ACG CCC ATC AAA AAC TTC         1187
Cys Gly Arg Asp Glu Tyr Leu Val Gly Glu Thr Pro Ile Lys Asn Phe
240                 245                 250                 255

CAG TGG GTG AGG CAC TGC CTC AAG AAC GGA GAA GAG ATT CAC GTG GTA         1235
Gln Trp Val Arg His Cys Leu Lys Asn Gly Glu Glu Ile His Val Val
                 260                 265                 270

CTG GAC ACG CCT CCA GAC CCG GCC CTA GAC GAG GTG AGG AAG GAA GAG         1283
Leu Asp Thr Pro Pro Asp Pro Ala Leu Asp Glu Val Arg Lys Glu Glu
             275                 280                 285

TGG CCG CTG GTG GAC GAC TGC ACG GGA GTC ACC GGC TAC CAT GAG CAG         1331
Trp Pro Leu Val Asp Asp Cys Thr Gly Val Thr Gly Tyr His Glu Gln
         290                 295                 300
```

| | | | | | | | | | | | | | | | | |
|---|---|---|---|---|---|---|---|---|---|---|---|---|---|---|---|---|
| CTT | ACC | ATC | CAC | GGC | AAG | GAC | CAC | GAG | AGT | GTG | TTC | ACC | GTG | TCC | CTG | 1379 |
| Leu | Thr | Ile | His | Gly | Lys | Asp | His | Glu | Ser | Val | Phe | Thr | Val | Ser | Leu | |
| | 305 | | | | 310 | | | | | 315 | | | | | | |
| TGG | GAC | TGC | GAC | CGC | AAG | TTC | AGG | GTC | AAG | ATC | AGA | GGC | ATT | GAT | ATC | 1427 |
| Trp | Asp | Cys | Asp | Arg | Lys | Phe | Arg | Val | Lys | Ile | Arg | Gly | Ile | Asp | Ile | |
| 320 | | | | | 325 | | | | | 330 | | | | | 335 | |
| CCC | GTC | CTG | CCT | CGG | AAC | ACC | GAC | CTC | ACA | GTT | TTT | GTA | GAG | GCA | AAC | 1475 |
| Pro | Val | Leu | Pro | Arg | Asn | Thr | Asp | Leu | Thr | Val | Phe | Val | Glu | Ala | Asn | |
| | | | | 340 | | | | | 345 | | | | | 350 | | |
| ATC | CAG | CAT | GGG | CAA | CAA | GTC | CTT | TGC | CAA | AGG | AGA | ACC | AGC | CCC | AAA | 1523 |
| Ile | Gln | His | Gly | Gln | Gln | Val | Leu | Cys | Gln | Arg | Arg | Thr | Ser | Pro | Lys | |
| | | | 355 | | | | | 360 | | | | | 365 | | | |
| CCC | TTC | ACA | GAG | GAG | GTG | CTG | TGG | AAT | GTG | TGG | CTT | GAG | TTC | AGT | ATC | 1571 |
| Pro | Phe | Thr | Glu | Glu | Val | Leu | Trp | Asn | Val | Trp | Leu | Glu | Phe | Ser | Ile | |
| | | 370 | | | | | 375 | | | | | 380 | | | | |
| AAA | ATC | AAA | GAC | TTG | CCC | AAA | GGG | GCT | CTA | CTG | AAC | CTC | CAG | ATC | TAC | 1619 |
| Lys | Ile | Lys | Asp | Leu | Pro | Lys | Gly | Ala | Leu | Leu | Asn | Leu | Gln | Ile | Tyr | |
| 385 | | | | | 390 | | | | | 395 | | | | | | |
| TGC | GGT | AAA | GCT | CCA | GCA | CTG | TCC | AGC | AAG | GCC | TCT | GCA | GAG | TCC | CCC | 1667 |
| Cys | Gly | Lys | Ala | Pro | Ala | Leu | Ser | Ser | Lys | Ala | Ser | Ala | Glu | Ser | Pro | |
| 400 | | | | | 405 | | | | | 410 | | | | | 415 | |
| AGT | TCT | GAG | TCC | AAG | GGC | AAA | GTT | CGG | CTT | CTC | TAT | TAT | GTG | AAC | CTG | 1715 |
| Ser | Ser | Glu | Ser | Lys | Gly | Lys | Val | Arg | Leu | Leu | Tyr | Tyr | Val | Asn | Leu | |
| | | | | 420 | | | | | 425 | | | | | 430 | | |
| CTG | CTG | ATA | GAC | CAC | CGT | TTC | CTC | CTG | CGC | CGT | GGA | GAA | TAC | GTC | CTC | 1763 |
| Leu | Leu | Ile | Asp | His | Arg | Phe | Leu | Leu | Arg | Arg | Gly | Glu | Tyr | Val | Leu | |
| | | | 435 | | | | | 440 | | | | | 445 | | | |
| CAC | ATG | TGG | CAG | ATA | TCT | GGG | AAG | GGA | GAA | GAC | CAA | GGA | AGC | TTC | AAT | 1811 |
| His | Met | Trp | Gln | Ile | Ser | Gly | Lys | Gly | Glu | Asp | Gln | Gly | Ser | Phe | Asn | |
| | | 450 | | | | | 455 | | | | | 460 | | | | |
| GCT | GAC | AAA | CTC | ACG | TCT | GCA | ACT | AAC | CCA | GAC | AAG | GAG | AAC | TCA | ATG | 1859 |
| Ala | Asp | Lys | Leu | Thr | Ser | Ala | Thr | Asn | Pro | Asp | Lys | Glu | Asn | Ser | Met | |
| 465 | | | | | 470 | | | | | 475 | | | | | | |
| TCC | ATC | TCC | ATT | CTT | CTG | GAC | AAT | TAC | TGC | CAC | CCG | ATA | GCC | CTG | CCT | 1907 |
| Ser | Ile | Ser | Ile | Leu | Leu | Asp | Asn | Tyr | Cys | His | Pro | Ile | Ala | Leu | Pro | |
| 480 | | | | | 485 | | | | | 490 | | | | | 495 | |
| AAG | CAT | CAG | CCC | ACC | CCT | GAC | CCG | GAA | GGG | GAC | CGG | GTT | CGA | GCA | GAA | 1955 |
| Lys | His | Gln | Pro | Thr | Pro | Asp | Pro | Glu | Gly | Asp | Arg | Val | Arg | Ala | Glu | |
| | | | | 500 | | | | | 505 | | | | | 510 | | |
| ATG | CCC | AAC | CAG | CTT | CGC | AAG | CAA | TTG | GAG | GCG | ATC | ATA | GCC | ACT | GAT | 2003 |
| Met | Pro | Asn | Gln | Leu | Arg | Lys | Gln | Leu | Glu | Ala | Ile | Ile | Ala | Thr | Asp | |
| | | | 515 | | | | | 520 | | | | | 525 | | | |
| CCA | CTT | AAC | CCT | CTC | ACA | GCA | GAG | GAC | AAA | GAA | TTG | CTC | TGG | CAT | TTT | 2051 |
| Pro | Leu | Asn | Pro | Leu | Thr | Ala | Glu | Asp | Lys | Glu | Leu | Leu | Trp | His | Phe | |
| | | 530 | | | | | 535 | | | | | 540 | | | | |
| AGA | TAC | GAA | AGC | CTT | AAG | CAC | CCA | AAA | GCA | TAT | CCT | AAG | CTA | TTT | AGT | 2099 |
| Arg | Tyr | Glu | Ser | Leu | Lys | His | Pro | Lys | Ala | Tyr | Pro | Lys | Leu | Phe | Ser | |
| 545 | | | | | 550 | | | | | 555 | | | | | | |
| TCA | GTG | AAA | TGG | GGA | CAG | CAA | GAA | ATT | GTG | GCC | AAA | ACA | TAC | CAA | TTG | 2147 |
| Ser | Val | Lys | Trp | Gly | Gln | Gln | Glu | Ile | Val | Ala | Lys | Thr | Tyr | Gln | Leu | |
| 560 | | | | | 565 | | | | | 570 | | | | | 575 | |
| TTG | GCC | AGA | AGG | GAA | GTC | TGG | GAT | CAA | AGT | GCT | TTG | GAT | GTT | GGG | TTA | 2195 |
| Leu | Ala | Arg | Arg | Glu | Val | Trp | Asp | Gln | Ser | Ala | Leu | Asp | Val | Gly | Leu | |
| | | | | 580 | | | | | 585 | | | | | 590 | | |
| ACA | ATG | CAG | CTC | CTG | GAC | TGC | AAC | TTC | TCA | GAT | GAA | AAT | GTA | AGA | GCC | 2243 |
| Thr | Met | Gln | Leu | Leu | Asp | Cys | Asn | Phe | Ser | Asp | Glu | Asn | Val | Arg | Ala | |
| | | | 595 | | | | | 600 | | | | | 605 | | | |
| ATT | GCA | GTT | CAG | AAA | CTG | GAG | AGC | TTG | GAG | GAC | GAT | GAT | GTT | CTG | CAT | 2291 |
| Ile | Ala | Val | Gln | Lys | Leu | Glu | Ser | Leu | Glu | Asp | Asp | Asp | Val | Leu | His | |
| | | 610 | | | | | 615 | | | | | 620 | | | | |

-continued

| | | | | | | | | | | | | | | | | |
|---|---|---|---|---|---|---|---|---|---|---|---|---|---|---|---|---|
| TAC | CTT | CTA | CAA | TTG | GTC | CAG | GCT | GTG | AAA | TTT | GAA | CCA | TAC | CAT | GAT | 2339 |
| Tyr | Leu | Leu | Gln | Leu | Val | Gln | Ala | Val | Lys | Phe | Glu | Pro | Tyr | His | Asp | |
| | 625 | | | | 630 | | | | | 635 | | | | | | |
| AGC | GCC | CTT | GCC | AGA | TTT | CTG | CTG | AAG | CGT | GGT | TTA | AGA | AAC | AAA | AGA | 2387 |
| Ser | Ala | Leu | Ala | Arg | Phe | Leu | Leu | Lys | Arg | Gly | Leu | Arg | Asn | Lys | Arg | |
| 640 | | | | | 645 | | | | | 650 | | | | | 655 | |
| ATT | GGT | CAC | TTT | TTG | TTT | TGG | TTC | TTG | AGA | AGT | GAG | ATA | GCC | CAG | TCC | 2435 |
| Ile | Gly | His | Phe | Leu | Phe | Trp | Phe | Leu | Arg | Ser | Glu | Ile | Ala | Gln | Ser | |
| | | | | 660 | | | | | 665 | | | | | 670 | | |
| AGA | CAC | TAT | CAG | CAG | AGG | TTC | GCT | GTG | ATT | CTG | GAA | GCC | TAT | CTG | AGG | 2483 |
| Arg | His | Tyr | Gln | Gln | Arg | Phe | Ala | Val | Ile | Leu | Glu | Ala | Tyr | Leu | Arg | |
| | | | 675 | | | | | 680 | | | | | 685 | | | |
| GGC | TGT | GGC | ACA | GCC | ATG | CTG | CAC | GAC | TTT | ACC | CAA | CAA | GTC | CAA | GTA | 2531 |
| Gly | Cys | Gly | Thr | Ala | Met | Leu | His | Asp | Phe | Thr | Gln | Gln | Val | Gln | Val | |
| | | 690 | | | | | 695 | | | | | 700 | | | | |
| ATC | GAG | ATG | TTA | CAA | AAA | GTC | ACC | CTT | GAT | ATT | AAA | TCG | CTC | TCT | GCT | 2579 |
| Ile | Glu | Met | Leu | Gln | Lys | Val | Thr | Leu | Asp | Ile | Lys | Ser | Leu | Ser | Ala | |
| | | 705 | | | | | 710 | | | | | 715 | | | | |
| GAA | AAG | TAT | GAC | GTC | AGT | TCC | CAA | GTT | ATT | TCA | CAA | CTT | AAA | CAA | AAG | 2627 |
| Glu | Lys | Tyr | Asp | Val | Ser | Ser | Gln | Val | Ile | Ser | Gln | Leu | Lys | Gln | Lys | |
| 720 | | | | | 725 | | | | | 730 | | | | | 735 | |
| CTT | GAA | AAC | CTG | CAG | AAT | TCT | CAA | CTC | CCC | GAA | AGC | TTT | AGA | GTT | CCA | 2675 |
| Leu | Glu | Asn | Leu | Gln | Asn | Ser | Gln | Leu | Pro | Glu | Ser | Phe | Arg | Val | Pro | |
| | | | | 740 | | | | | 745 | | | | | 750 | | |
| TAT | GAT | CCT | GGA | CTG | AAA | GCA | GGA | GCG | CTG | GCA | ATT | GAA | AAA | TGT | AAA | 2723 |
| Tyr | Asp | Pro | Gly | Leu | Lys | Ala | Gly | Ala | Leu | Ala | Ile | Glu | Lys | Cys | Lys | |
| | | | 755 | | | | | 760 | | | | | 765 | | | |
| GTA | ATG | GCC | TCC | AAG | AAA | AAA | CCA | CTA | TGG | CTT | GAG | TTT | AAA | TGT | GCC | 2771 |
| Val | Met | Ala | Ser | Lys | Lys | Lys | Pro | Leu | Trp | Leu | Glu | Phe | Lys | Cys | Ala | |
| | | 770 | | | | | 775 | | | | | 780 | | | | |
| GAT | CCT | ACA | GCC | CTA | TCA | AAT | GAA | ACA | ATT | GGA | ATT | ATC | TTT | AAA | CAT | 2819 |
| Asp | Pro | Thr | Ala | Leu | Ser | Asn | Glu | Thr | Ile | Gly | Ile | Ile | Phe | Lys | His | |
| | 785 | | | | | 790 | | | | | 795 | | | | | |
| GGT | GAT | GAT | CTG | CGC | CAA | GAC | ATG | CTT | ATT | TTA | CAG | ATT | CTA | CGA | ATC | 2867 |
| Gly | Asp | Asp | Leu | Arg | Gln | Asp | Met | Leu | Ile | Leu | Gln | Ile | Leu | Arg | Ile | |
| 800 | | | | | 805 | | | | | 810 | | | | | 815 | |
| ATG | GAG | TCT | ATT | TGG | GAG | ACT | GAA | TCT | TTG | GAT | CTA | TGC | CTC | CTG | CCA | 2915 |
| Met | Glu | Ser | Ile | Trp | Glu | Thr | Glu | Ser | Leu | Asp | Leu | Cys | Leu | Leu | Pro | |
| | | | | 820 | | | | | 825 | | | | | 830 | | |
| TAT | GGT | TGC | ATT | TCA | ACT | GGT | GAC | AAA | ATA | GGA | ATG | ATC | GAG | ATT | GTG | 2963 |
| Tyr | Gly | Cys | Ile | Ser | Thr | Gly | Asp | Lys | Ile | Gly | Met | Ile | Glu | Ile | Val | |
| | | | 835 | | | | | 840 | | | | | 845 | | | |
| AAA | GAC | GCC | ACG | ACA | ATT | GCC | AAA | ATT | CAG | CAA | AGC | ACA | GTG | GGC | AAC | 3011 |
| Lys | Asp | Ala | Thr | Thr | Ile | Ala | Lys | Ile | Gln | Gln | Ser | Thr | Val | Gly | Asn | |
| | | 850 | | | | | 855 | | | | | 860 | | | | |
| ACG | GGA | GCA | TTT | AAA | GAT | GAA | GTC | CTG | AAT | CAC | TGG | CTC | AAA | GAA | AAA | 3059 |
| Thr | Gly | Ala | Phe | Lys | Asp | Glu | Val | Leu | Asn | His | Trp | Leu | Lys | Glu | Lys | |
| 865 | | | | | 870 | | | | | 875 | | | | | | |
| TCC | CCT | ACT | GAA | GAA | AAG | TTT | CAG | GCA | GCA | GTG | GAG | AGA | TTT | GTT | TAT | 3107 |
| Ser | Pro | Thr | Glu | Glu | Lys | Phe | Gln | Ala | Ala | Val | Glu | Arg | Phe | Val | Tyr | |
| 880 | | | | | 885 | | | | | 890 | | | | | 895 | |
| TCC | TGT | GCA | GGC | TAC | TGT | GTG | GCA | ACC | TTT | GTT | CTT | GGA | ATA | GGC | GAC | 3155 |
| Ser | Cys | Ala | Gly | Tyr | Cys | Val | Ala | Thr | Phe | Val | Leu | Gly | Ile | Gly | Asp | |
| | | | | 900 | | | | | 905 | | | | | 910 | | |
| AGA | CAC | AAT | GAC | AAT | ATT | ATG | ATC | ACC | GAG | ACA | GGA | AAC | CTA | TTT | CAT | 3203 |
| Arg | His | Asn | Asp | Asn | Ile | Met | Ile | Thr | Glu | Thr | Gly | Asn | Leu | Phe | His | |
| | | | | 915 | | | | | 920 | | | | | 925 | | |
| ATT | GAC | TTC | GGG | CAC | ATT | CTT | GGG | AAT | TAC | AAA | AGT | TTC | CTG | GGC | ATT | 3251 |
| Ile | Asp | Phe | Gly | His | Ile | Leu | Gly | Asn | Tyr | Lys | Ser | Phe | Leu | Gly | Ile | |
| | | | 930 | | | | | 935 | | | | | 940 | | | |

```
AAT  AAA  GAG  AGA  GTG  CCA  TTT  GTG  CTA  ACC  CCT  GAC  TTC  CTC  TTT  GTG      3299
Asn  Lys  Glu  Arg  Val  Pro  Phe  Val  Leu  Thr  Pro  Asp  Phe  Leu  Phe  Val
945                           950                      955

ATG  GGA  ACT  TCT  GGA  AAG  AAG  ACA  AGC  CCA  CAC  TTC  CAG  AAA  TTT  CAG      3347
Met  Gly  Thr  Ser  Gly  Lys  Lys  Thr  Ser  Pro  His  Phe  Gln  Lys  Phe  Gln
960                           965                      970                     975

GAC  ATC  TGT  GTT  AAG  GCT  TAT  CTA  GCC  CTT  CGT  CAT  CAC  ACA  AAC  CTA      3395
Asp  Ile  Cys  Val  Lys  Ala  Tyr  Leu  Ala  Leu  Arg  His  His  Thr  Asn  Leu
                              980                      985                     990

CTG  ATC  ATC  CTG  TTC  TCC  ATG  ATG  CTG  ATG  ACA  GGA  ATG  CCC  CAG  TTA      3443
Leu  Ile  Ile  Leu  Phe  Ser  Met  Met  Leu  Met  Thr  Gly  Met  Pro  Gln  Leu
                    995                       1000                     1005

ACA  AGC  AAA  GAA  GAC  ATT  GAA  TAT  ATC  CGG  GAT  GCC  CTC  ACA  GTG  GGG      3491
Thr  Ser  Lys  Glu  Asp  Ile  Glu  Tyr  Ile  Arg  Asp  Ala  Leu  Thr  Val  Gly
               1010                      1015                     1020

AAA  AAT  GAG  GAG  GAT  GCT  AAA  AAG  TAT  TTT  CTT  GAT  CAG  ATC  GAA  GTT      3539
Lys  Asn  Glu  Glu  Asp  Ala  Lys  Lys  Tyr  Phe  Leu  Asp  Gln  Ile  Glu  Val
               1025                      1030                     1035

TGG  CAG  AGA  CAA  AGG  ATG  GAC  TGT  GCA  GTT  TAATTGGTTT  CTACATCTTG            3589
Trp  Gln  Arg  Gln  Arg  Met  Asp  Cys  Ala  Val
1040                      1045

TTCTTGGCAT  CAAACAAGGA  GAGAAACATT  CAGCCTAATA  CTTTAGGCTA  GAATCAAAAA             3649

CAAGTTAGTG  TTCTATGGTT  TAAATTAGCA  TAGCAATCAT  CGAACTTGGA  TTTCAAATGC             3709

AATAGACATT  GTGAAAGCTG  GCATTTCAGA  AGTATAGCTC  TTTTCCTACC  TGAACTCTTC             3769

CCTGGAGAAA  AGATGTTGGC  ATTGCTGATT  GTTTGGTTAA  GCAATGTCCA  GTGCTAGGAT             3829

TATTTGCAGG  TTTGGTTTTT  TCTCATTTGT  CTGTGGCATT  GGAGAATATT  CTCGGTTTAA             3889

ACAGACTAAT  GACTTCCTTA  TTGTCCCTGA  TATTTGACT   ATCTTACTAT  TGAGTGCTTC             3949

TGGAAATTCT  TTGGAATAAT  TGATGACATC  TATTTTCATC  TGGGTTTAGT  CTCAATTTTG             4009

GTTATCTTTG  TGTTCCTCAA  GCTCTTTAAA  GAAAAAGATG  TAATCGTTGT  AACCTTTGTC             4069

TCATTCCTTA  AATGATGCTT  CCAAACATCT  CCTTAGTGTC  TGCAGGTGTT  AGTGGTGTGC             4129

TAAAA                                                                              4134
```

( 2 ) INFORMATION FOR SEQ ID NO: 2:

( i ) SEQUENCE CHARACTERISTICS:
        ( A ) LENGTH: 1049 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Glu  Leu  Ile  Pro  Ile  Glu  Phe  Val  Leu  Pro  Thr  Ser  Gln  Arg  Lys
1                   5                        10                      15

Cys  Lys  Ser  Pro  Glu  Thr  Ala  Leu  Leu  His  Val  Ala  Gly  His  Gly  Asn
               20                       25                      30

Val  Glu  Gln  Met  Lys  Ala  Gln  Val  Trp  Leu  Arg  Ala  Leu  Glu  Thr  Ser
                    35                       40                      45

Trp  Arg  Gly  Leu  Leu  Pro  Pro  Ala  Gly  Thr  Ala  Ser  Leu  Pro  Pro  Ala
          50                       55                      60

Leu  Ser  Glu  Glu  Gly  Gln  Trp  Tyr  Glu  Ile  Tyr  Asp  Lys  Tyr  Gln  Val
65                       70                      75                           80

Val  Gln  Thr  Leu  Asp  Cys  Leu  Arg  Tyr  Trp  Lys  Ala  Thr  His  Arg  Ser
                    85                       90                      95

Pro  Gly  Gln  Ile  His  Leu  Val  Gln  Arg  His  Pro  Pro  Ser  Glu  Glu  Ser
```

-continued

|     |     |     | 100 |     |     |     |     | 105 |     |     |     |     | 110 |     |
| --- | --- | --- | --- | --- | --- | --- | --- | --- | --- | --- | --- | --- | --- | --- |

Gln Ala Phe Gln Arg Gln Leu Thr Ala Leu Ile Gly Tyr Asp Val Thr
        115                 120                 125

Asp Val Ser Asn Val His Asp Asp Glu Leu Glu Phe Thr Arg Arg Gly
130                 135                 140

Leu Val Thr Pro Arg Met Ala Glu Val Ala Ser Arg Asp Pro Lys Leu
145                 150                 155                 160

Tyr Ala Met His Pro Trp Val Thr Ser Lys Pro Leu Pro Glu Tyr Leu
                165                 170                 175

Trp Lys Lys Ile Ala Asn Asn Cys Ile Phe Ile Val Ile His Arg Ser
            180                 185                 190

Thr Thr Ser Gln Thr Ile Lys Val Ser Pro Asp Asp Thr Pro Gly Ala
            195                 200                 205

Ile Leu Gln Ser Phe Phe Thr Lys Met Ala Lys Lys Lys Ser Leu Met
        210                 215                 220

Asp Ile Pro Glu Ser Gln Ser Glu Gln Asp Phe Val Leu Arg Val Cys
225                 230                 235                 240

Gly Arg Asp Glu Tyr Leu Val Gly Glu Thr Pro Ile Lys Asn Phe Gln
                245                 250                 255

Trp Val Arg His Cys Leu Lys Asn Gly Glu Glu Ile His Val Val Leu
            260                 265                 270

Asp Thr Pro Pro Asp Pro Ala Leu Asp Glu Val Arg Lys Glu Glu Trp
        275                 280                 285

Pro Leu Val Asp Asp Cys Thr Gly Val Thr Gly Tyr His Glu Gln Leu
        290                 295                 300

Thr Ile His Gly Lys Asp His Glu Ser Val Phe Thr Val Ser Leu Trp
305                 310                 315                 320

Asp Cys Asp Arg Lys Phe Arg Val Lys Ile Arg Gly Ile Asp Ile Pro
                325                 330                 335

Val Leu Pro Arg Asn Thr Asp Leu Thr Val Phe Val Glu Ala Asn Ile
            340                 345                 350

Gln His Gly Gln Gln Val Leu Cys Gln Arg Arg Thr Ser Pro Lys Pro
            355                 360                 365

Phe Thr Glu Glu Val Leu Trp Asn Val Trp Leu Glu Phe Ser Ile Lys
370                 375                 380

Ile Lys Asp Leu Pro Lys Gly Ala Leu Leu Asn Leu Gln Ile Tyr Cys
385                 390                 395                 400

Gly Lys Ala Pro Ala Leu Ser Ser Lys Ala Ser Ala Glu Ser Pro Ser
                405                 410                 415

Ser Glu Ser Lys Gly Lys Val Arg Leu Leu Tyr Tyr Val Asn Leu Leu
            420                 425                 430

Leu Ile Asp His Arg Phe Leu Leu Arg Arg Gly Glu Tyr Val Leu His
            435                 440                 445

Met Trp Gln Ile Ser Gly Lys Gly Glu Asp Gln Gly Ser Phe Asn Ala
450                 455                 460

Asp Lys Leu Thr Ser Ala Thr Asn Pro Asp Lys Glu Asn Ser Met Ser
465                 470                 475                 480

Ile Ser Ile Leu Leu Asp Asn Tyr Cys His Pro Ile Ala Leu Pro Lys
                485                 490                 495

His Gln Pro Thr Pro Asp Pro Glu Gly Asp Arg Val Arg Ala Glu Met
            500                 505                 510

Pro Asn Gln Leu Arg Lys Gln Leu Glu Ala Ile Ile Ala Thr Asp Pro
            515                 520                 525

| | | | | | | | | | | | | | | |
|---|---|---|---|---|---|---|---|---|---|---|---|---|---|---|
|Leu|Asn|Pro|Leu|Thr|Ala|Glu|Asp|Lys|Glu|Leu|Leu|Trp|His|Phe|Arg|
| |530| | | |535| | | | |540| | | | | |
|Tyr|Glu|Ser|Leu|Lys|His|Pro|Lys|Ala|Tyr|Pro|Lys|Leu|Phe|Ser|Ser|
|545| | | | |550| | | | |555| | | | |560|
|Val|Lys|Trp|Gly|Gln|Glu|Ile|Val|Ala|Lys|Thr|Tyr|Gln|Leu| | |
| | | | |565| | | |570| | | | |575| | |
|Ala|Arg|Arg|Glu|Val|Trp|Asp|Gln|Ser|Ala|Leu|Asp|Val|Gly|Leu|Thr|
| | | |580| | | |585| | | | |590| | | |
|Met|Gln|Leu|Leu|Asp|Cys|Asn|Phe|Ser|Asp|Glu|Asn|Val|Arg|Ala|Ile|
| | |595| | | |600| | | | |605| | | | |
|Ala|Val|Gln|Lys|Leu|Glu|Ser|Leu|Glu|Asp|Asp|Val|Leu|His|Tyr| |
| |610| | | | |615| | | |620| | | | | |
|Leu|Leu|Gln|Leu|Val|Gln|Ala|Val|Lys|Phe|Glu|Pro|Tyr|His|Asp|Ser|
|625| | | | |630| | | |635| | | | | |640|
|Ala|Leu|Ala|Arg|Phe|Leu|Leu|Lys|Arg|Gly|Leu|Arg|Asn|Lys|Arg|Ile|
| | | | |645| | | |650| | | | |655| | |
|Gly|His|Phe|Leu|Phe|Trp|Phe|Leu|Arg|Ser|Glu|Ile|Ala|Gln|Ser|Arg|
| | | |660| | | |665| | | | |670| | | |
|His|Tyr|Gln|Gln|Arg|Phe|Ala|Val|Ile|Leu|Glu|Ala|Tyr|Leu|Arg|Gly|
| | |675| | | | |680| | | | |685| | | |
|Cys|Gly|Thr|Ala|Met|Leu|His|Asp|Phe|Thr|Gln|Val|Gln|Val|Ile| |
| |690| | | | |695| | | |700| | | | | |
|Glu|Met|Leu|Gln|Lys|Val|Thr|Leu|Asp|Ile|Lys|Ser|Leu|Ser|Ala|Glu|
|705| | | | |710| | | |715| | | | | |720|
|Lys|Tyr|Asp|Val|Ser|Ser|Gln|Val|Ile|Ser|Gln|Leu|Lys|Gln|Lys|Leu|
| | | | |725| | | |730| | | | |735| | |
|Glu|Asn|Leu|Gln|Asn|Ser|Gln|Leu|Pro|Glu|Ser|Phe|Arg|Val|Pro|Tyr|
| | | |740| | | |745| | | | |750| | | |
|Asp|Pro|Gly|Leu|Lys|Ala|Gly|Ala|Leu|Ala|Ile|Glu|Lys|Cys|Lys|Val|
| | |755| | | |760| | | | |765| | | | |
|Met|Ala|Ser|Lys|Lys|Lys|Pro|Leu|Trp|Leu|Glu|Phe|Lys|Cys|Ala|Asp|
| |770| | | | |775| | | | |780| | | | |
|Pro|Thr|Ala|Leu|Ser|Asn|Glu|Thr|Ile|Gly|Ile|Ile|Phe|Lys|His|Gly|
|785| | | | |790| | | |795| | | | | |800|
|Asp|Asp|Leu|Arg|Gln|Asp|Met|Leu|Ile|Leu|Gln|Ile|Leu|Arg|Ile|Met|
| | | | |805| | | |810| | | | |815| | |
|Glu|Ser|Ile|Trp|Glu|Thr|Glu|Ser|Leu|Asp|Leu|Cys|Leu|Leu|Pro|Tyr|
| | | |820| | | |825| | | | |830| | | |
|Gly|Cys|Ile|Ser|Thr|Gly|Asp|Lys|Ile|Gly|Met|Ile|Glu|Ile|Val|Lys|
| | |835| | | |840| | | | |845| | | | |
|Asp|Ala|Thr|Thr|Ile|Ala|Lys|Ile|Gln|Gln|Ser|Thr|Val|Gly|Asn|Thr|
| |850| | | | |855| | | | |860| | | | |
|Gly|Ala|Phe|Lys|Asp|Glu|Val|Leu|Asn|His|Trp|Leu|Lys|Glu|Lys|Ser|
|865| | | | |870| | | |875| | | | | |880|
|Pro|Thr|Glu|Glu|Lys|Phe|Gln|Ala|Ala|Val|Glu|Arg|Phe|Val|Tyr|Ser|
| | | | |885| | | |890| | | | |895| | |
|Cys|Ala|Gly|Tyr|Cys|Val|Ala|Thr|Phe|Val|Leu|Gly|Ile|Gly|Asp|Arg|
| | | |900| | | |905| | | | |910| | | |
|His|Asn|Asp|Asn|Ile|Met|Ile|Thr|Glu|Thr|Gly|Asn|Leu|Phe|His|Ile|
| | |915| | | |920| | | | |925| | | | |
|Asp|Phe|Gly|His|Ile|Leu|Gly|Asn|Tyr|Lys|Ser|Phe|Leu|Gly|Ile|Asn|
| |930| | | | |935| | | | |940| | | | |
|Lys|Glu|Arg|Val|Pro|Phe|Val|Leu|Thr|Pro|Asp|Phe|Leu|Phe|Val|Met|
|945| | | | |950| | | |955| | | | | |960|

|  |  |  |  |  |  |  |  |  |  |  |  |  |  |
|---|---|---|---|---|---|---|---|---|---|---|---|---|---|
| Gly | Thr | Ser | Gly | Lys | Lys | Thr | Ser | Pro | His | Phe | Gln | Lys | Phe | Gln | Asp |
|  |  |  |  | 965 |  |  |  |  | 970 |  |  |  |  | 975 |
| Ile | Cys | Val | Lys | Ala | Tyr | Leu | Ala | Leu | Arg | His | His | Thr | Asn | Leu | Leu |
|  |  |  | 980 |  |  |  |  | 985 |  |  |  |  | 990 |  |  |
| Ile | Ile | Leu | Phe | Ser | Met | Met | Leu | Met | Thr | Gly | Met | Pro | Gln | Leu | Thr |
|  |  |  | 995 |  |  |  |  | 1000 |  |  |  |  | 1005 |  |  |
| Ser | Lys | Glu | Asp | Ile | Glu | Tyr | Ile | Arg | Asp | Ala | Leu | Thr | Val | Gly | Lys |
|  |  | 1010 |  |  |  | 1015 |  |  |  |  | 1020 |  |  |  |  |
| Asn | Glu | Glu | Asp | Ala | Lys | Lys | Tyr | Phe | Leu | Asp | Gln | Ile | Glu | Val | Trp |
| 1025 |  |  |  |  | 1030 |  |  |  |  | 1035 |  |  |  |  | 1040 |
| Gln | Arg | Gln | Arg | Met | Asp | Cys | Ala | Val |
|  |  |  |  | 1045 |  |  |  |  |

( 2 ) INFORMATION FOR SEQ ID NO: 3:

( i ) SEQUENCE CHARACTERISTICS:
        ( A ) LENGTH: 4137 base pairs
        ( B ) TYPE: nucleic acid
        ( C ) STRANDEDNESS: both
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 423..3572

( x i ) SEQUENCE DESCRIPTION: SEQ ID NO: 3:

| | |
|---|---|
| GAATTCGGCA CGAGCACTTC CTTCTCGGCT AGATTATCTG AAACTGTTGT CGGTTCTTGA | 60 |
| GATGATACTA CCACCGAATG TCTGTGTTTC ATTGTCTAGT CCAACCTGTA TTGTGGATAT | 120 |
| CTACAACGTT CCGGCAATAG TTTTGCAGGT GCATCACATT TTTGTTTTG TTTTGGGAGG | 180 |
| AAAAGGGAGG GCACGGCAGC CAGGCTTCAT ATTCCTACAA GTGCATGCTT CAAGATTACT | 240 |
| GTACTTACAG TGTTTCCAAC ATCTTCTCAT AAAAGGGGAA AGCTTCATAG CCTCAACCAT | 300 |
| GAAGGAAACC AGTCGCATAG GGCATGGAGC TGGAGAACTA TAAACAGCCC GTGGTGCTGA | 360 |
| GAGAGGACAA CTGCCGAAGG CGCCGGAGGA TGAAGCCGCG CAGTGCTGCC AGCCTGTCCT | 420 |

| | | | | | | | | | | | | | | | |
|---|---|---|---|---|---|---|---|---|---|---|---|---|---|---|---|
| CC | ATG | GAG | CTC | ATC | CCC | ATC | GAG | TTC | GTG | CTG | CCC | ACC | AGC | CAG | CGC | 467 |
|  | Met | Glu | Leu | Ile | Pro | Ile | Glu | Phe | Val | Leu | Pro | Thr | Ser | Gln | Arg |  |
|  | 1050 |  |  |  |  | 1055 |  |  |  |  | 1060 |  |  |  |  |  |
| AAA | TGC | AAG | AGC | CCC | GAA | ACG | GCG | CTG | CTG | CAC | GTG | GCC | GGC | CAC | GGC | 515 |
| Lys | Cys | Lys | Ser | Pro | Glu | Thr | Ala | Leu | Leu | His | Val | Ala | Gly | His | Gly |  |
| 1065 |  |  |  |  | 1070 |  |  |  |  | 1075 |  |  |  |  | 1080 |  |
| AAC | GTG | GAG | CAG | ATG | AAG | GCC | CAG | GTG | TGG | CTG | CGA | GCG | CTG | GAG | ACC | 563 |
| Asn | Val | Glu | Gln | Met | Lys | Ala | Gln | Val | Trp | Leu | Arg | Ala | Leu | Glu | Thr |  |
|  |  |  |  | 1085 |  |  |  |  | 1090 |  |  |  |  | 1095 |  |  |
| AGC | GTG | GCG | GCG | GAC | TTC | TAC | CAC | CGG | CTG | GGA | CCG | CAT | CAC | TTC | CTC | 611 |
| Ser | Val | Ala | Ala | Asp | Phe | Tyr | His | Arg | Leu | Gly | Pro | His | His | Phe | Leu |  |
|  |  |  |  | 1100 |  |  |  |  | 1105 |  |  |  |  | 1110 |  |  |
| CTG | CTC | TAT | CAG | AAG | AAG | GGG | CAG | TGG | TAC | GAG | ATC | TAC | GAC | AAG | TAC | 659 |
| Leu | Leu | Tyr | Gln | Lys | Lys | Gly | Gln | Trp | Tyr | Glu | Ile | Tyr | Asp | Lys | Tyr |  |
|  |  |  | 1115 |  |  |  |  | 1120 |  |  |  |  | 1125 |  |  |  |
| CAG | GTG | GTG | CAG | ACT | CTG | GAC | TGC | CTG | CGC | TAC | TGG | AAG | GCC | ACG | CAC | 707 |
| Gln | Val | Val | Gln | Thr | Leu | Asp | Cys | Leu | Arg | Tyr | Trp | Lys | Ala | Thr | His |  |
|  |  | 1130 |  |  |  |  | 1135 |  |  |  |  | 1140 |  |  |  |  |
| CGG | AGC | CCG | GGC | CAG | ATC | CAC | CTG | GTG | CAG | CGG | CAC | CCG | CCC | TCC | GAG | 755 |
| Arg | Ser | Pro | Gly | Gln | Ile | His | Leu | Val | Gln | Arg | His | Pro | Pro | Ser | Glu |  |
| 1145 |  |  |  |  | 1150 |  |  |  |  | 1155 |  |  |  |  | 1160 |  |

```
GAG  TCC  CAA  GCC  TTC  CAG  CGG  CAG  CTC  ACG  GCG  CTG  ATT  GGC  TAT  GAC        803
Glu  Ser  Gln  Ala  Phe  Gln  Arg  Gln  Leu  Thr  Ala  Leu  Ile  Gly  Tyr  Asp
          1165                1170                     1175

GTC  ACT  GAC  GTC  AGC  AAC  GTG  CAC  GAC  GAT  GAG  CTG  GAG  TTC  ACG  CGC        851
Val  Thr  Asp  Val  Ser  Asn  Val  His  Asp  Asp  Glu  Leu  Glu  Phe  Thr  Arg
          1180                1185                     1190

CGT  GGC  TTG  GTG  ACC  CCG  CGC  ATG  GCG  GAG  GTG  GCC  AGC  CGC  GAC  CCC        899
Arg  Gly  Leu  Val  Thr  Pro  Arg  Met  Ala  Glu  Val  Ala  Ser  Arg  Asp  Pro
          1195                1200                     1205

AAG  CTC  TAC  GCC  ATG  CAC  CCG  TGG  GTG  ACG  TCC  AAG  CCC  CTC  CCG  GAG        947
Lys  Leu  Tyr  Ala  Met  His  Pro  Trp  Val  Thr  Ser  Lys  Pro  Leu  Pro  Glu
          1210                1215                     1220

TAC  CTG  TGG  AAG  AAG  ATT  GCC  AAC  AAC  TGC  ATC  TTC  ATC  GTC  ATT  CAC        995
Tyr  Leu  Trp  Lys  Lys  Ile  Ala  Asn  Asn  Cys  Ile  Phe  Ile  Val  Ile  His
1225                1230                     1235                     1240

CGC  AGC  ACC  ACC  AGC  CAG  ACC  ATT  AAG  GTC  TCA  CCC  GAC  GAC  ACC  CCC       1043
Arg  Ser  Thr  Thr  Ser  Gln  Thr  Ile  Lys  Val  Ser  Pro  Asp  Asp  Thr  Pro
          1245                1250                     1255

GGC  GCC  ATC  CTG  CAG  AGC  TTC  TTC  ACC  AAG  ATG  GCC  AAG  AAG  AAA  TCT       1091
Gly  Ala  Ile  Leu  Gln  Ser  Phe  Phe  Thr  Lys  Met  Ala  Lys  Lys  Lys  Ser
          1260                1265                     1270

CTG  ATG  GAT  ATT  CCC  GAA  AGC  CAA  AGC  GAA  CAG  GAT  TTT  GTG  CTG  CGC       1139
Leu  Met  Asp  Ile  Pro  Glu  Ser  Gln  Ser  Glu  Gln  Asp  Phe  Val  Leu  Arg
          1275                1280                     1285

GTC  TGT  GGC  CGG  GAT  GAG  TAC  CTG  GTG  GGC  GAA  ACG  CCC  ATC  AAA  AAC       1187
Val  Cys  Gly  Arg  Asp  Glu  Tyr  Leu  Val  Gly  Glu  Thr  Pro  Ile  Lys  Asn
          1290                1295                     1300

TTC  CAG  TGG  GTG  AGG  CAC  TGC  CTC  AAG  AAC  GGA  GAA  GAG  ATT  CAC  GTG       1235
Phe  Gln  Trp  Val  Arg  His  Cys  Leu  Lys  Asn  Gly  Glu  Glu  Ile  His  Val
1305                1310                     1315                     1320

GTA  CTG  GAC  ACG  CCT  CCA  GAC  CCG  GCC  CTA  GAC  GAG  GTG  AGG  AAG  GAA       1283
Val  Leu  Asp  Thr  Pro  Pro  Asp  Pro  Ala  Leu  Asp  Glu  Val  Arg  Lys  Glu
          1325                1330                     1335

GAG  TGG  CCG  CTG  GTG  GAC  GAC  TGC  ACG  GGA  GTC  ACC  GGC  TAC  CAT  GAG       1331
Glu  Trp  Pro  Leu  Val  Asp  Asp  Cys  Thr  Gly  Val  Thr  Gly  Tyr  His  Glu
          1340                1345                     1350

CAG  CTT  ACC  ATC  CAC  GGC  AAG  GAC  CAC  GAG  AGT  GTG  TTC  ACC  GTG  TCC       1379
Gln  Leu  Thr  Ile  His  Gly  Lys  Asp  His  Glu  Ser  Val  Phe  Thr  Val  Ser
          1355                1360                     1365

CTG  TGG  GAC  TGC  GAC  CGC  AAG  TTC  AGG  GTC  AAG  ATC  AGA  GGC  ATT  GAT       1427
Leu  Trp  Asp  Cys  Asp  Arg  Lys  Phe  Arg  Val  Lys  Ile  Arg  Gly  Ile  Asp
          1370                1375                     1380

ATC  CCC  GTC  CTG  CCT  CGG  AAC  ACC  GAC  CTC  ACA  GTT  TTT  GTA  GAG  GCA       1475
Ile  Pro  Val  Leu  Pro  Arg  Asn  Thr  Asp  Leu  Thr  Val  Phe  Val  Glu  Ala
1385                1390                     1395                     1400

AAC  ATC  CAG  CAT  GGG  CAA  CAA  GTC  CTT  TGC  CAA  AGG  AGA  ACC  AGC  CCC       1523
Asn  Ile  Gln  His  Gly  Gln  Gln  Val  Leu  Cys  Gln  Arg  Arg  Thr  Ser  Pro
          1405                1410                     1415

AAA  CCC  TTC  ACA  GAG  GAG  GTG  CTG  TGG  AAT  GTG  TGG  CTT  GAG  TTC  AGT       1571
Lys  Pro  Phe  Thr  Glu  Glu  Val  Leu  Trp  Asn  Val  Trp  Leu  Glu  Phe  Ser
          1420                1425                     1430

ATC  AAA  ATC  AAA  GAC  TTG  CCC  AAA  GGG  GCT  CTA  CTG  AAC  CTC  CAG  ATC       1619
Ile  Lys  Ile  Lys  Asp  Leu  Pro  Lys  Gly  Ala  Leu  Leu  Asn  Leu  Gln  Ile
          1435                1440                     1445

TAC  TGC  GGT  AAA  GCT  CCA  GCA  CTG  TCC  AGC  AAG  GCC  TCT  GCA  GAG  TCC       1667
Tyr  Cys  Gly  Lys  Ala  Pro  Ala  Leu  Ser  Ser  Lys  Ala  Ser  Ala  Glu  Ser
          1450                1455                     1460

CCC  AGT  TCT  GAG  TCC  AAG  GGC  AAA  GTT  CGG  CTT  CTC  TAT  TAT  GTG  AAC       1715
Pro  Ser  Ser  Glu  Ser  Lys  Gly  Lys  Val  Arg  Leu  Leu  Tyr  Tyr  Val  Asn
1465                1470                     1475                     1480
```

```
CTG CTG CTG ATA GAC CAC CGT TTC CTC CTG CGC CGT GGA GAA TAC GTC      1763
Leu Leu Leu Ile Asp His Arg Phe Leu Leu Arg Arg Gly Glu Tyr Val
            1485                1490                1495

CTC CAC ATG TGG CAG ATA TCT GGG AAG GGA GAA GAC CAA GGA AGC TTC      1811
Leu His Met Trp Gln Ile Ser Gly Lys Gly Glu Asp Gln Gly Ser Phe
        1500                1505                1510

AAT GCT GAC AAA CTC ACG TCT GCA ACT AAC CCA GAC AAG GAG AAC TCA      1859
Asn Ala Asp Lys Leu Thr Ser Ala Thr Asn Pro Asp Lys Glu Asn Ser
    1515                1520                1525

ATG TCC ATC TCC ATT CTT CTG GAC AAT TAC TGC CAC CCG ATA GCC CTG      1907
Met Ser Ile Ser Ile Leu Leu Asp Asn Tyr Cys His Pro Ile Ala Leu
1530                1535                1540

CCT AAG CAT CAG CCC ACC CCT GAC CCG GAA GGG GAC CGG GTT CGA GCA      1955
Pro Lys His Gln Pro Thr Pro Asp Pro Glu Gly Asp Arg Val Arg Ala
1545                1550                1555                1560

GAA ATG CCC AAC CAG CTT CGC AAG CAA TTG GAG GCG ATC ATA GCC ACT      2003
Glu Met Pro Asn Gln Leu Arg Lys Gln Leu Glu Ala Ile Ile Ala Thr
            1565                1570                1575

GAT CCA CTT AAC CCT CTC ACA GCA GAG GAC AAA GAA TTG CTC TGG CAT      2051
Asp Pro Leu Asn Pro Leu Thr Ala Glu Asp Lys Glu Leu Leu Trp His
        1580                1585                1590

TTT AGA TAC GAA AGC CTT AAG CAC CCA AAA GCA TAT CCT AAG CTA TTT      2099
Phe Arg Tyr Glu Ser Leu Lys His Pro Lys Ala Tyr Pro Lys Leu Phe
    1595                1600                1605

AGT TCA GTG AAA TGG GGA CAG CAA GAA ATT GTG GCC AAA ACA TAC CAA      2147
Ser Ser Val Lys Trp Gly Gln Gln Glu Ile Val Ala Lys Thr Tyr Gln
1610                1615                1620

TTG TTG GCC AGA AGG GAA GTC TGG GAT CAA AGT GCT TTG GAT GTT GGG      2195
Leu Leu Ala Arg Arg Glu Val Trp Asp Gln Ser Ala Leu Asp Val Gly
1625                1630                1635                1640

TTA ACA ATG CAG CTC CTG GAC TGC AAC TTC TCA GAT GAA AAT GTA AGA      2243
Leu Thr Met Gln Leu Leu Asp Cys Asn Phe Ser Asp Glu Asn Val Arg
            1645                1650                1655

GCC ATT GCA GTT CAG AAA CTG GAG AGC TTG GAG GAC GAT GAT GTT CTG      2291
Ala Ile Ala Val Gln Lys Leu Glu Ser Leu Glu Asp Asp Asp Val Leu
        1660                1665                1670

CAT TAC CTT CTA CAA TTG GTC CAG GCT GTG AAA TTT GAA CCA TAC CAT      2339
His Tyr Leu Leu Gln Leu Val Gln Ala Val Lys Phe Glu Pro Tyr His
    1675                1680                1685

GAT AGC GCC CTT GCC AGA TTT CTG CTG AAG CGT GGT TTA AGA AAC AAA      2387
Asp Ser Ala Leu Ala Arg Phe Leu Leu Lys Arg Gly Leu Arg Asn Lys
1690                1695                1700

AGA ATT GGT CAC TTT TTG TTT TGG TTC TTG AGA AGT GAG ATA GCC CAG      2435
Arg Ile Gly His Phe Leu Phe Trp Phe Leu Arg Ser Glu Ile Ala Gln
1705                1710                1715                1720

TCC AGA CAC TAT CAG CAG AGG TTC GCT GTG ATT CTG GAA GCC TAT CTG      2483
Ser Arg His Tyr Gln Gln Arg Phe Ala Val Ile Leu Glu Ala Tyr Leu
            1725                1730                1735

AGG GGC TGT GGC ACA GCC ATG CTG CAC GAC TTT ACC CAA CAA GTC CAA      2531
Arg Gly Cys Gly Thr Ala Met Leu His Asp Phe Thr Gln Gln Val Gln
        1740                1745                1750

GTA ATC GAG ATG TTA CAA AAA GTC ACC CTT GAT ATT AAA TCG CTC TCT      2579
Val Ile Glu Met Leu Gln Lys Val Thr Leu Asp Ile Lys Ser Leu Ser
    1755                1760                1765

GCT GAA AAG TAT GAC GTC AGT TCC CAA GTT ATT TCA CAA CTT AAA CAA      2627
Ala Glu Lys Tyr Asp Val Ser Ser Gln Val Ile Ser Gln Leu Lys Gln
1770                1775                1780

AAG CTT GAA AAC CTG CAG AAT TCT CAA CTC CCC GAA AGC TTT AGA GTT      2675
Lys Leu Glu Asn Leu Gln Asn Ser Gln Leu Pro Glu Ser Phe Arg Val
1785                1790                1795                1800
```

```
CCA TAT GAT CCT GGA CTG AAA GCA GGA GCG CTG GCA ATT GAA AAA TGT      2723
Pro Tyr Asp Pro Gly Leu Lys Ala Gly Ala Leu Ala Ile Glu Lys Cys
            1805                1810                1815

AAA GTA ATG GCC TCC AAG AAA AAA CCA CTA TGG CTT GAG TTT AAA TGT      2771
Lys Val Met Ala Ser Lys Lys Lys Pro Leu Trp Leu Glu Phe Lys Cys
        1820                1825                1830

GCC GAT CCT ACA GCC CTA TCA AAT GAA ACA ATT GGA ATT ATC TTT AAA      2819
Ala Asp Pro Thr Ala Leu Ser Asn Glu Thr Ile Gly Ile Ile Phe Lys
            1835                1840                1845

CAT GGT GAT GAT CTG CGC CAA GAC ATG CTT ATT TTA CAG ATT CTA CGA      2867
His Gly Asp Asp Leu Arg Gln Asp Met Leu Ile Leu Gln Ile Leu Arg
        1850                1855                1860

ATC ATG GAG TCT ATT TGG GAG ACT GAA TCT TTG GAT CTA TGC CTC CTG      2915
Ile Met Glu Ser Ile Trp Glu Thr Glu Ser Leu Asp Leu Cys Leu Leu
1865                1870                1875                1880

CCA TAT GGT TGC ATT TCA ACT GGT GAC AAA ATA GGA ATG ATC GAG ATT      2963
Pro Tyr Gly Cys Ile Ser Thr Gly Asp Lys Ile Gly Met Ile Glu Ile
                1885                1890                1895

GTG AAA GAC GCC ACG ACA ATT GCC AAA ATT CAG CAA AGC ACA GTG GGC      3011
Val Lys Asp Ala Thr Thr Ile Ala Lys Ile Gln Gln Ser Thr Val Gly
            1900                1905                1910

AAC ACG GGA GCA TTT AAA GAT GAA GTC CTG AAT CAC TGG CTC AAA GAA      3059
Asn Thr Gly Ala Phe Lys Asp Glu Val Leu Asn His Trp Leu Lys Glu
        1915                1920                1925

AAA TCC CCT ACT GAA GAA AAG TTT CAG GCA GCA GTG GAG AGA TTT GTT      3107
Lys Ser Pro Thr Glu Glu Lys Phe Gln Ala Ala Val Glu Arg Phe Val
    1930                1935                1940

TAT TCC TGT GCA GGC TAC TGT GTG GCA ACC TTT GTT CTT GGA ATA GGC      3155
Tyr Ser Cys Ala Gly Tyr Cys Val Ala Thr Phe Val Leu Gly Ile Gly
1945                1950                1955                1960

GAC AGA CAC AAT GAC AAT ATT ATG ATC ACC GAG ACA GGA AAC CTA TTT      3203
Asp Arg His Asn Asp Asn Ile Met Ile Thr Glu Thr Gly Asn Leu Phe
            1965                1970                1975

CAT ATT GAC TTC GGG CAC ATT CTT GGG AAT TAC AAA AGT TTC CTG GGC      3251
His Ile Asp Phe Gly His Ile Leu Gly Asn Tyr Lys Ser Phe Leu Gly
        1980                1985                1990

ATT AAT AAA GAG AGA GTG CCA TTT GTG CTA ACC CCT GAC TTC CTC TTT      3299
Ile Asn Lys Glu Arg Val Pro Phe Val Leu Thr Pro Asp Phe Leu Phe
    1995                2000                2005

GTG ATG GGA ACT TCT GGA AAG AAG ACA AGC CCA CAC TTC CAG AAA TTT      3347
Val Met Gly Thr Ser Gly Lys Lys Thr Ser Pro His Phe Gln Lys Phe
2010                2015                2020

CAG GAC ATC TGT GTT AAG GCT TAT CTA GCC CTT CGT CAT CAC ACA AAC      3395
Gln Asp Ile Cys Val Lys Ala Tyr Leu Ala Leu Arg His His Thr Asn
2025                2030                2035                2040

CTA CTG ATC ATC CTG TTC TCC ATG ATG CTG ATG ACA GGA ATG CCC CAG      3443
Leu Leu Ile Ile Leu Phe Ser Met Met Leu Met Thr Gly Met Pro Gln
            2045                2050                2055

TTA ACA AGC AAA GAA GAC ATT GAA TAT ATC CGG GAT GCC CTC ACA GTG      3491
Leu Thr Ser Lys Glu Asp Ile Glu Tyr Ile Arg Asp Ala Leu Thr Val
        2060                2065                2070

GGG AAA AAT GAG GAG GAT GCT AAA AAG TAT TTT CTT GAT CAG ATC GAA      3539
Gly Lys Asn Glu Glu Asp Ala Lys Lys Tyr Phe Leu Asp Gln Ile Glu
    2075                2080                2085

GTT TGG CAG AGA CAA AGG ATG GAC TGT GCA GTT TAATTGGTTT CTACATCTTG    3592
Val Trp Gln Arg Gln Arg Met Asp Cys Ala Val
2090                2095

TTCTTGGCAT CAAACAAGGA GAGAAACATT CAGCCTAATA CTTTAGGCTA GAATCAAAAA    3652

CAAGTTAGTG TTCTATGGTT TAAATTAGCA TAGCAATCAT CGAACTTGGA TTTCAAATGC    3712
```

| | | | | | |
|---|---|---|---|---|---|
| AATAGACATT | GTGAAAGCTG | GCATTTCAGA | AGTATAGCTC | TTTTCCTACC | TGAACTCTTC | 3772 |
| CCTGGAGAAA | AGATGTTGGC | ATTGCTGATT | GTTTGGTTAA | GCAATGTCCA | GTGCTAGGAT | 3832 |
| TATTTGCAGG | TTTGGTTTTT | TCTCATTTGT | CTGTGGCATT | GGAGAATATT | CTCGGTTTAA | 3892 |
| ACAGACTAAT | GACTTCCTTA | TTGTCCCTGA | TATTTTGACT | ATCTTACTAT | TGAGTGCTTC | 3952 |
| TGGAAATTCT | TTGGAATAAT | TGATGACATC | TATTTTCATC | TGGGTTTAGT | CTCAATTTTG | 4012 |
| GTTATCTTTG | TGTTCCTCAA | GCTCTTTAAA | GAAAAGATG | TAATCGTTGT | AACCTTTGTC | 4072 |
| TCATTCCTTA | AATGATGCTT | CCAAACATCT | CCTTAGTGTC | TGCAGGTGTT | AGTGGTGTGC | 4132 |
| TAAAA | | | | | | 4137 |

(2) INFORMATION FOR SEQ ID NO: 4:

(i) SEQUENCE CHARACTERISTICS:
        (A) LENGTH: 1050 amino acids
        (B) TYPE: amino acid
        (D) TOPOLOGY: linear (ii) MOLECULE TYPE: protein (xi) SEQUENCE DESCRIPTION: SEQ ID NO: 4:

```
Met  Glu  Leu  Ile  Pro  Ile  Glu  Phe  Val  Leu  Pro  Thr  Ser  Gln  Arg  Lys
  1              5                      10                      15

Cys  Lys  Ser  Pro  Glu  Thr  Ala  Leu  Leu  His  Val  Ala  Gly  His  Gly  Asn
             20                      25                      30

Val  Glu  Gln  Met  Lys  Ala  Gln  Val  Trp  Leu  Arg  Ala  Leu  Glu  Thr  Ser
         35                      40                      45

Val  Ala  Ala  Asp  Phe  Tyr  His  Arg  Leu  Gly  Pro  His  His  Phe  Leu  Leu
     50                      55                      60

Leu  Tyr  Gln  Lys  Lys  Gly  Gln  Trp  Tyr  Glu  Ile  Tyr  Asp  Lys  Tyr  Gln
 65                      70                      75                      80

Val  Val  Gln  Thr  Leu  Asp  Cys  Leu  Arg  Tyr  Trp  Lys  Ala  Thr  His  Arg
                 85                      90                      95

Ser  Pro  Gly  Gln  Ile  His  Leu  Val  Gln  Arg  His  Pro  Pro  Ser  Glu  Glu
                100                     105                     110

Ser  Gln  Ala  Phe  Gln  Arg  Gln  Leu  Thr  Ala  Leu  Ile  Gly  Tyr  Asp  Val
            115                     120                     125

Thr  Asp  Val  Ser  Asn  Val  His  Asp  Asp  Glu  Leu  Glu  Phe  Thr  Arg  Arg
        130                     135                     140

Gly  Leu  Val  Thr  Pro  Arg  Met  Ala  Glu  Val  Ala  Ser  Arg  Asp  Pro  Lys
145                     150                     155                     160

Leu  Tyr  Ala  Met  His  Pro  Trp  Val  Thr  Ser  Lys  Pro  Leu  Pro  Glu  Tyr
                165                     170                     175

Leu  Trp  Lys  Lys  Ile  Ala  Asn  Asn  Cys  Ile  Phe  Ile  Val  Ile  His  Arg
            180                     185                     190

Ser  Thr  Thr  Ser  Gln  Thr  Ile  Lys  Val  Ser  Pro  Asp  Asp  Thr  Pro  Gly
        195                     200                     205

Ala  Ile  Leu  Gln  Ser  Phe  Phe  Thr  Lys  Met  Ala  Lys  Lys  Ser  Leu
        210                     215                     220

Met  Asp  Ile  Pro  Glu  Ser  Gln  Ser  Glu  Gln  Asp  Phe  Val  Leu  Arg  Val
225                     230                     235                     240

Cys  Gly  Arg  Asp  Glu  Tyr  Leu  Val  Gly  Glu  Thr  Pro  Ile  Lys  Asn  Phe
                245                     250                     255

Gln  Trp  Val  Arg  His  Cys  Leu  Lys  Asn  Gly  Glu  Glu  Ile  His  Val  Val
                260                     265                     270
```

```
Leu Asp Thr Pro Pro Asp Pro Ala Leu Asp Glu Val Arg Lys Glu Glu
        275             280                 285
Trp Pro Leu Val Asp Asp Cys Thr Gly Val Thr Gly Tyr His Glu Gln
    290             295             300
Leu Thr Ile His Gly Lys Asp His Glu Ser Val Phe Thr Val Ser Leu
305                 310             315                     320
Trp Asp Cys Asp Arg Lys Phe Arg Val Lys Ile Arg Gly Ile Asp Ile
                325             330              335
Pro Val Leu Pro Arg Asn Thr Asp Leu Thr Val Phe Val Glu Ala Asn
            340             345             350
Ile Gln His Gly Gln Gln Val Leu Cys Gln Arg Arg Thr Ser Pro Lys
        355             360             365
Pro Phe Thr Glu Glu Val Leu Trp Asn Val Trp Leu Glu Phe Ser Ile
    370             375             380
Lys Ile Lys Asp Leu Pro Lys Gly Ala Leu Leu Asn Leu Gln Ile Tyr
385             390             395                     400
Cys Gly Lys Ala Pro Ala Leu Ser Ser Lys Ala Ser Ala Glu Ser Pro
            405             410             415
Ser Ser Glu Ser Lys Gly Lys Val Arg Leu Leu Tyr Tyr Val Asn Leu
        420             425             430
Leu Leu Ile Asp His Arg Phe Leu Leu Arg Arg Gly Glu Tyr Val Leu
        435             440             445
His Met Trp Gln Ile Ser Gly Lys Gly Glu Asp Gln Gly Ser Phe Asn
    450             455             460
Ala Asp Lys Leu Thr Ser Ala Thr Asn Pro Asp Lys Glu Asn Ser Met
465             470             475                     480
Ser Ile Ser Ile Leu Leu Asp Asn Tyr Cys His Pro Ile Ala Leu Pro
            485             490             495
Lys His Gln Pro Thr Pro Asp Pro Glu Gly Asp Arg Val Arg Ala Glu
        500             505             510
Met Pro Asn Gln Leu Arg Lys Gln Leu Glu Ala Ile Ile Ala Thr Asp
    515             520             525
Pro Leu Asn Pro Leu Thr Ala Glu Asp Lys Glu Leu Leu Trp His Phe
    530             535             540
Arg Tyr Glu Ser Leu Lys His Pro Lys Ala Tyr Pro Lys Leu Phe Ser
545             550             555                     560
Ser Val Lys Trp Gly Gln Gln Glu Ile Val Ala Lys Thr Tyr Gln Leu
            565             570             575
Leu Ala Arg Arg Glu Val Trp Asp Gln Ser Ala Leu Asp Val Gly Leu
            580             585             590
Thr Met Gln Leu Leu Asp Cys Asn Phe Ser Asp Glu Asn Val Arg Ala
        595             600             605
Ile Ala Val Gln Lys Leu Glu Ser Leu Glu Asp Asp Asp Val Leu His
    610             615             620
Tyr Leu Leu Gln Leu Val Gln Ala Val Lys Phe Glu Pro Tyr His Asp
625             630             635                     640
Ser Ala Leu Ala Arg Phe Leu Leu Lys Arg Gly Leu Arg Asn Lys Arg
            645             650             655
Ile Gly His Phe Leu Phe Trp Phe Leu Arg Ser Glu Ile Ala Gln Ser
        660             665             670
Arg His Tyr Gln Gln Arg Phe Ala Val Ile Leu Glu Ala Tyr Leu Arg
        675             680             685
Gly Cys Gly Thr Ala Met Leu His Asp Phe Thr Gln Gln Val Gln Val
        690             695             700
```

-continued

| | | | | | | | | | | | | | | |
|---|---|---|---|---|---|---|---|---|---|---|---|---|---|---|
| Ile | Glu | Met | Leu | Gln | Lys | Val | Thr | Leu | Asp | Ile | Lys | Ser | Leu | Ser | Ala |
| 705 | | | | 710 | | | | | 715 | | | | | 720 |
| Glu | Lys | Tyr | Asp | Val | Ser | Ser | Gln | Val | Ile | Ser | Gln | Leu | Lys | Gln | Lys |
| | | | | 725 | | | | 730 | | | | | 735 | | |
| Leu | Glu | Asn | Leu | Gln | Asn | Ser | Gln | Leu | Pro | Glu | Ser | Phe | Arg | Val | Pro |
| | | | 740 | | | | 745 | | | | | 750 | | | |
| Tyr | Asp | Pro | Gly | Leu | Lys | Ala | Gly | Ala | Leu | Ala | Ile | Glu | Lys | Cys | Lys |
| | | 755 | | | | | 760 | | | | | 765 | | | |
| Val | Met | Ala | Ser | Lys | Lys | Lys | Pro | Leu | Trp | Leu | Glu | Phe | Lys | Cys | Ala |
| | 770 | | | | | 775 | | | | 780 | | | | | |
| Asp | Pro | Thr | Ala | Leu | Ser | Asn | Glu | Thr | Ile | Gly | Ile | Ile | Phe | Lys | His |
| 785 | | | | | 790 | | | | 795 | | | | | | 800 |
| Gly | Asp | Asp | Leu | Arg | Gln | Asp | Met | Leu | Ile | Leu | Gln | Ile | Leu | Arg | Ile |
| | | | | 805 | | | | | 810 | | | | | 815 | |
| Met | Glu | Ser | Ile | Trp | Glu | Thr | Glu | Ser | Leu | Asp | Leu | Cys | Leu | Leu | Pro |
| | | | 820 | | | | | 825 | | | | | 830 | | |
| Tyr | Gly | Cys | Ile | Ser | Thr | Gly | Asp | Lys | Ile | Gly | Met | Ile | Glu | Ile | Val |
| | | 835 | | | | | 840 | | | | | 845 | | | |
| Lys | Asp | Ala | Thr | Thr | Ile | Ala | Lys | Ile | Gln | Gln | Ser | Thr | Val | Gly | Asn |
| | 850 | | | | | 855 | | | | | 860 | | | | |
| Thr | Gly | Ala | Phe | Lys | Asp | Glu | Val | Leu | Asn | His | Trp | Leu | Lys | Glu | Lys |
| 865 | | | | | 870 | | | | | 875 | | | | | 880 |
| Ser | Pro | Thr | Glu | Glu | Lys | Phe | Gln | Ala | Ala | Val | Glu | Arg | Phe | Val | Tyr |
| | | | | 885 | | | | | 890 | | | | | 895 | |
| Ser | Cys | Ala | Gly | Tyr | Cys | Val | Ala | Thr | Phe | Val | Leu | Gly | Ile | Gly | Asp |
| | | | 900 | | | | | 905 | | | | | 910 | | |
| Arg | His | Asn | Asp | Asn | Ile | Met | Ile | Thr | Glu | Thr | Gly | Asn | Leu | Phe | His |
| | | 915 | | | | | 920 | | | | | 925 | | | |
| Ile | Asp | Phe | Gly | His | Ile | Leu | Gly | Asn | Tyr | Lys | Ser | Phe | Leu | Gly | Ile |
| | 930 | | | | | 935 | | | | | 940 | | | | |
| Asn | Lys | Glu | Arg | Val | Pro | Phe | Val | Leu | Thr | Pro | Asp | Phe | Leu | Phe | Val |
| 945 | | | | | 950 | | | | | 955 | | | | | 960 |
| Met | Gly | Thr | Ser | Gly | Lys | Lys | Thr | Ser | Pro | His | Phe | Gln | Lys | Phe | Gln |
| | | | | 965 | | | | | 970 | | | | | 975 | |
| Asp | Ile | Cys | Val | Lys | Ala | Tyr | Leu | Ala | Leu | Arg | His | His | Thr | Asn | Leu |
| | | | 980 | | | | | 985 | | | | | 990 | | |
| Leu | Ile | Ile | Leu | Phe | Ser | Met | Met | Leu | Met | Thr | Gly | Met | Pro | Gln | Leu |
| | | | 995 | | | | 1000 | | | | | 1005 | | | |
| Thr | Ser | Lys | Glu | Asp | Ile | Glu | Tyr | Ile | Arg | Asp | Ala | Leu | Thr | Val | Gly |
| | | 1010 | | | | 1015 | | | | | 1020 | | | | |
| Lys | Asn | Glu | Glu | Asp | Ala | Lys | Lys | Tyr | Phe | Leu | Asp | Gln | Ile | Glu | Val |
| 1025 | | | | | 1030 | | | | 1035 | | | | | | 1040 |
| Trp | Gln | Arg | Gln | Arg | Met | Asp | Cys | Ala | Val | | | | | | |
| | | | | 1045 | | | | | 1050 | | | | | | |

( 2 ) INFORMATION FOR SEQ ID NO: 5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

Asn   Ser   Gln   Leu   Pro   Glu   Ser   Phe   Arg   Val   Pro   Tyr   Asp   Pro   Gly

-continued (2) INFORMATION FOR SEQ ID NO: 6:

(i) SEQUENCE CHARACTERISTICS:
        (A) LENGTH:7 amino acids
        (B) TYPE: amino acid
        (D) TOPOLOGY: linear (ii) MOLECULE TYPE: protein (xi) SEQUENCE DESCRIPTION: SEQ ID NO: 6:

```
Lys  Asn  Gly  Asp  Asp  Leu  Arg
1                  5
```

(2) INFORMATION FOR SEQ ID NO: 7:

(i) SEQUENCE CHARACTERISTICS:
        (A) LENGTH:5 amino acids
        (B) TYPE: amino acid
        (D) TOPOLOGY: linear (ii) MOLECULE TYPE: protein (xi) SEQUENCE DESCRIPTION: SEQ ID NO: 7:

```
His  Ile  Asp  Phe  Gly
1                  5
```

CLONING, EXPRESSION AND CHARACTERIZATION OF A NOVEL FORM OF PHOSPHATIDYLINOSITOL-3-KINASE

RELATED APPLICATION

This application is a national stage application of PCT/EP95/03990 filed Oct. 10, 1995 under 35 USC 371.

BACKGROUND OF THE INVENTION

The present invention concerns a new phosphatidylinositol-3-kinase (PI3Kγ), a nucleic acid which codes for it, an antibody directed against the protein as well as the diagnostic and therapeutic use of the protein, of the nucleic acid and of the antibody.

Phosphatidylinositol-kinases belong, together with specific phospholipases, to an enzyme group which catalyses the formation of intracellular messenger substances from the membrane lipid phosphatidyl inositol (PI). The activity of these enzymes is regulated by extracellular effectors such as hormones, growth factors and neurotransmitters. It is assumed that the PI dependent messenger substances are involved among other processes in the regulation of important cells functions such as cell proliferation, secretion of cellular constituents, endocytotic processes, the targetted movement of certain cells, controlled changes of the cytoskeleton. Correspondingly the physiological importance of the PI kinases and phospholipases correlates with a series of disease states involving changes of the functions of these enzymes.

From various experimental results it is possible to conclude that the product of the reaction catalysed by PI3 kinase, PI-3,4,5 triphosphate plays an important role in the regulation of the following physiological cell functions:
Regulation of cell proliferation and cell differentiation by PI 3 kinase Mitogens such as growth factors and cytokines generally lead to a stimulation of the PI 3 kinase activity in cells capable of division. The oncogenic transformation of cells is also often accompanied by an increase in the measurable PI 3 kinase activity (Varticovski et al., Biochim. Biophys. Acta 1226, 1–11 (1994), Berggren et al., Cancer Research 53, 4297–4302 (1993), Soldi et al., Oncogene 9, 2253–2260 (1994)). Inhibitors of PI 3 kinase are able to inhibit the PDGF-stimulated growth of normal connective tissue cells or smooth muscle cells and the proliferation of src-supratransformed fibroblasts (cancer cells) (Berggren et al., Cancer Research 53, 4297–4302 (1993), Vlahos et al., J.Biol.Chem. 269, 5241–5248 (1994)). Berggren et al., have speculated that the tumoristatic effect of ether lipid analogues is mainly based on their inhibitory action on PI 3 kinase.

The differentiation of the nerve cell line PC12 is suppressed by wortmannin an inhibitor of PI 3 kinase (Kimurea et al., J.Biol.Chem. 269, 18961–18967 (1994)). These findings as well as a clinical study in which there was shown to be a selective loss of PI 3 kinase activity in the brain of Alzheimer patients (Bothmer et al., Dementia 5, 6–11 (1994)) indicate that the enzyme has an important function in the formation and maintenance of nerve tissue.
Regulation of cytoskeletal-dependent processes by PI 3 kinase Microscopically visible changes of cells often progress with the involvement of the cytoskeleton. A series of results shows that at least some of these processes are regulated by PI 3 kinase and its enzymatic products (PI3,4,5,$P_3$, PI3,4$P_2$ and PI3P). Thus the membrane ruffling of epidermal cells induced by insulin or PDGF can be suppressed by the PI 3 kinase inhibitor wortmannin (Kotani et al., EMBO J. 13, 2313–2321 (1994), Wennström et al., Curr. Biol. 4, 385–393 (1994)).

Basophilic leucocytes are able to secrete histamine—a mediator of inflammations and allergic symptoms. The cytoskeleton of the cells is involved in this secretion process. Yano et al., J. Biol.Chem. 268, 25846–25856 (1993) were able to show that the antibody-induced histamine secretion can in turn be inhibited by the PI 3 kinase inhibitor wortmannin i.e. it is apparently controlled by 3-phosphorylated phosphoinositides.
Involvement of PI 3 kinase in intracellular transport processes Investigations on yeast mutants show that one form of PI 3 kinase (Vps 34) is involved in these organisms in the selective distribution of proteins towards the yeast vacuoles (Schu et al., Science 260, 88–91 (1993)). Similar mechanisms may be the basis of the insulin-stimulated translocation of glucose transport protein (GLUT 4) from the interior of the cell to the plasma membrane (Kanai et al., Biochem. Biophys.Res.Commun. 195, 762–768 (1993)). This important process in various organs is also inhibited by wortmannin and apparently involves PI 3 kinase.
Inhibition of the $O_2^-$ production in neutrophilic granulocytes Granulocytes produce superoxide anions ($O_2^-$) with the aim of destroying phagocytised foreign cells. This process is stimulated by the chemoattractant fMLP. The blocking of the fMLP-induced $O_2^-$ formation by wortmannin indicates a regulatory function of a PI 3 kinase species in this important process for the immune response of the body.

The above-mentioned results underline the central importance of PI 3 kinase and 3-phosphorylated inositol lipids in the regulation of important cell functions. Acquired or inherited defects of the said cell functions are undoubtedly the underlying cause of important clinical syndromes. Examples are: cancer, arteriosclerosis, immunopathies, skin diseases (such as psoriasis), degenerative diseases of the nervous system.

Since Pi 3 kinase is an essential element in the regulation of the said cell functions it is very probable that some of the clinical syndromes are due to malfunctions of PI 3 kinase species. The clinical study on PI 3 kinase in the brain of Alzheimer patients, the findings on the role of PI 3 kinase in the formation of the allergy inducer histamine and also the cancerostatic effect of PI 3 kinase-inhibiting ether lipids point in this direction.

A central concern of cell biology is to discover the mechanisms of intracellular signal transmission and the messenger substances that are involved. The final goal of these investigations is to selectively influence cell functions in a medical sense.

SUMMARY OF THE INVENTION

The present application describes the identification, cloning, expression and c harac terization of a new species of PI 3 kinase. This new species is activated by G protein subunits and hence differs from the previous species PI3Kα (Hiles et al., Cell 70 (1992) 419–429) and PI3Kβ (Hu et al., J.Mol.Cell. Biol. 13, (1993), 7677–7688) cloned from mammalian cells and from the PI3K-Vps34 from yeast (Schu et al., supra and Herman et al., Cell 64 (1991), 425–438) with regard to the regulation mechanism. The functional differences between the known enzymes PI3Kα and PI3Kβ on the one hand as well as the enzyme PI3Kγ according to the invention on the other hand are reflected in differences in the sequences of the important regulatory domains of the enzyme.

Hence a subject matter of the invention is a protein with phosphatidylinositol-3-kinase activity which is characterized in that it comprises
a) the amino acid sequence shown in SEQ ID NO. 2
b) the amino acid sequence shown in SEQ ID NO. 4 or
c) variants of the sequence from (a).

The PI3Kγ according to the invention is preferably a protein obtainable from humans i.e. it is the protein shown in SEQ ID NO. 1 and No. 2, the protein shown in SEQ ID NO. 3 and NO. 4 or a naturally occurring human variant thereof.

The invention also concerns a new protein which comprises parts of the amino acid sequence shown in SEQ ID NO. 1 and 2 or SEQ ID NO. 3 and 4. The invention preferably concerns a PI3K which comprises the amino acid sequence shown in SEQ ID NO. 1 and 2 or the amino acid sequence shown in SEQ ID NO. 3 and 4; it can, however, also contain variants of this sequence. The term "variant" within the sense of the present invention is understood as sequences which differ from the amino acid sequence shown in SEQ ID NO. 1 and 2 or in SEQ ID NO. 3 and 4 by substitution, deletion or/and insertion of individual amino acids or short sections of amino acids.

The term "variant" includes naturally occurring allelic variations of PI3Kγ as well as proteins produced by recombinant DNA technology (in particular by in vitro mutagenesis with the aid of chemically synthesized oligonucleotides) which, with regard to their biological or/and immunological activity, essentially correspond to the protein shown in SEQ ID NO. 1 and 2 or to the protein shown in SEQ ID NO. 3 and 4.

A preferred characteristic of proteins according to the invention is that at the amino acid level they have a homology of at least 80% particularly preferably of 90% and most preferably of 95% to the amino acid sequence shown in SEQ ID NO. 1 and 2 or to the amino acid sequences shown in SEQ ID NO. 3 and 4.

The amino acid sequence shown in SEQ ID NO. 1 and 2 represents a whole PI3Kγ. This protein has 1049 amino acids and has a molecular mass of ca. 120 kDa. The amino acid sequence shown in SEQ ID NO. 3 and 4 represents a PI3Kγ with 1050 amino acids.

The amino acid sequence of PI3Kγ has a homology of 19 to 39% to the sequences of other known PI3K such as human PI3Kα (36% homology), human PI3Kβ (33.5% homology) and PI3KVps34 from yeast (27.7%). The most highly conserved region in this group of enzymes are the 400 C-terminal amino acid residues which presumably contain the kinase domain. There is no significant homology between PI3Kγ and the other enzymes in the amino-terminal region which is known to be responsible for the binding of PI3Kα and β-enzyme subunits to the regulatory and adaptory subunits p85α and p85β (Dhand et al., EMBO J. 13 (1994), 511–521).

PI3Kγ can be detected in the cell as a 110 kDa protein by immunoprecipitation and Western blot analysis of U937 and K562 cells using antipeptide antisera. A Northern blot analysis showed a 5.3 kb long mRNA in several different tissue types.

A further subject matter of the present invention is a nucleic acid which codes for a phosphatidylinositol-3-kinase or parts thereof according to the invention. This nucleic acid can for example be genomic DNA, cDNA or RNA. It is preferably a recombinant DNA molecule.

Another subject matter of the invention is a nucleic acid which contains
a) the coding sequence shown in SEQ ID NO. 1
b) the protein-coding sequence shown in SEQ ID NO. 3
c) a nucleic acid sequence corresponding to the sequence from (a) or (b) within the scope of the degeneracy of the genetic code or
d) a sequence hybridizing with the sequences from (a), (b) and/or (c) under stringent hybridization conditions.

Stringent hybridization conditions within the sense of the present invention are understood as a hybridization which also still occurs after washing at 55° C., preferably at 62° C., particularly preferably at 68° C. in an aqueous low salt buffer (e.g. 0.2×SSC, 0.1% SDS) (see also Sambrook et al. (1989) Molecular Cloning, A Laboratory Manual).

The invention also concerns nucleic acids which contain at least a 20 nucleotide long section of the sequence shown in SEQ ID NO. 1 or SEQ ID NO. 3. This section preferably has a specific nucleotide sequence for the PI3Kγ. These nucleic acids are especially suitable for the production of therapeutically applicable antisense nucleic acids which are preferably up to 50 nucleotides long.

Yet a further subject matter of the invention is a vector which contains at least one copy of a nucleic acid or a part thereof according to the invention. The vector can be capable of replication in eukaryotes or prokaryotes. It can be a vector which can be integrated into the genome of the host cell e.g. bacteriophage lambda, or a vector which is present extrachromosomally (e.g. a plasmid). The vector according to the invention can be obtained by subcloning the PI3Kγ DNA into a basic vector. Such basic vectors in particular vectors containing the necessary elements for protein expression are familiar to a person skilled in the art.

When a nucleic acid coding for PI3Kγ is cloned it is possible to construct an expression vector which can be made to express in a suitable host cell to form the protein according to the invention. Preferred host cells are microorganisms such as *E. coli* or yeast and also higher cells (e.g. mammalian or insect cells). Preferred expression vectors are e.g. plasmids, bacteriophage lambda for prokaryotes, yeast vectors or viral vectors for higher cells (e.g. SV40, vaccinia, baculorivuses). With regard to the expression of a nucleic acid coding for PI3Kγ particular reference is made to the methods mentioned in Sambrook et al. (1989) supra.

A specific example of a system suitable for the expression of PI3Kγ is the expression as a GST fusion protein in Sf9-insect cells using baculovectors according to the method described by Davis et al. (Biotechnology 11 (1993), 933–936).

A further subject matter of the present invention is a cell which is transformed with a nucleic acid according to the invention or a vector according to the invention. The cell can be a eukaryotic as well as a prokaryotic cell. Methods for the transformation of cells with nucleic acids are general state of the art and do not therefore need to be elucidated in more detail.

The use of the PI3Kγ protein or fragments of this protein as an immunogen for the production of antibodies is also a subject matter of the present invention. In this case the antibodies can be produced in the usual manner by immunizing experimental animals with the complete PI3Kγ protein or fragments thereof and subsequently isolating the resulting polyclonal antisera. The method of Köhler and Milstein or further developments thereof can be used to obtain monoclonal antibodies in a known manner from the antibody-producing cells of the experimental animals by cell fusion. It is also possible to produce human monoclonal antibodies.

Hence a further subject matter of the present invention is an antibody against a protein with phosphatidyl-inositol-3- kinase activity which is specific for phosphatidylinositol-3-kinase γ and does not exhibit any cross-reaction with other phosphatidylinositol-3-kinases. Such an antibody can for example be obtained by using a PI3Kγ-specific peptide sequence as the immunogen e.g. a peptide sequence which corresponds to the amino acids 741 to 755 of the amino acid sequence shown in SEQ ID NO. 1 and 2 or to the amino acids 742 to 756 of the amino acid sequence shown in SEQ ID NO. 3 and 4.

The provision of PI3 kinase γ, a nucleic acid which codes for it and an antibody which is directed towards it creates the basis for a specific search for effectors of this protein. The target for these substances should be the regulatory domains of the enzyme which are located in the region of the amino acid residues 1 to 700 of the amino acid sequences shown in SEQ ID NO. 1 and 2 or SEQ ID NO. 3 and 4. Substances which, via this region of the protein, have an inhibitory or activating effect on the activity are able to selectively influence the cell functions regulated by PI3Kγ. Consequently they can be used for the treatment of corresponding clinical pictures. In the case of clinical pictures which are due to a loss of PI3Kγ it may be possible to carry out a gene therapy treatment in which a nucleic acid coding for PI3Kγ optionally together with a nucleic acid which codes for the activating G proteins is transferred by means of vectors e.g. viral vectors into the appropriate target tissue.

Moreover the results that have been presented form the basis for a specific diagnosis of diseases which are causally linked to changes in PI3Kγ activity. These investigations can be carried out with the aid of specific nucleic acid probes for tests at the DNA level i.e. at the gene or transcription level or with the aid of antibodies against PI3Kγ for tests at the protein level.

Hence the present invention also concerns a pharmaceutical composition which comprises a PI3Kγ protein, an antibody directed towards it or a nucleic acid which codes for it as the active component optionally together with standard pharmaceutical auxiliary substances, carrier substances, fillers and diluents.

The pharmaceutical composition according to the invention can be used in particular to influence cell proliferation, receptor-mediated signal transmission, the structure of the cell membrane, the secretion of histamines, the differentiation of nerve cells, glucose transport and anti-lipolysis. Furthermore it can also be used in connection with the therapy of Alzheimer's disease.

The invention is elucidated in more detail by the following examples, figures and sequence protocols.

DETAILED DESCRIPTION

SEQ ID NO. 1 shows a nucleic acid sequence which contains genetic information coding for PI3Kγ and SEQ ID NO. 2 shows the amino acid sequence of a PI3Kγ.

SEQ ID NO: 3 shows a nucleic acid sequence which contains genetic information coding for a further PI3Kγ and SEQ ID NO. 4 shows the amino acid sequence of a further PI3Kγ.

EXAMPLE 1

Isolation of PI3Kγ cDNA

In order to isolate cDNA sequences which code for new PI3K a human bone marrow cDNA library was screened using the polymerase chain reaction (PCR). For this degenerate oligonucleotide primers were used corresponding to the amino acid sequences KNGDDLR [SEQ ID NO:6] and HIDFG [SEQ ID NO:7]. A 402 bp long fragment was obtained. This fragment was subcloned and sequenced.

Several overlapping clones from a human U937 cDNA library were isolated using this PCR fragment as a probe. The largest clone contained the nucleic acid sequence shown in SEQ ID NO. 1 with an open reading frame which codes for a protein with 1049 amino acids (SEQ ID NO. 2). This protein named PI3Kγ has a molecular mass of approximately 120 kDa.

A further PI3Kγ sequence which was obtained from a cDNA library is shown in SEQ ID NO. 3 and codes for a protein with 1050 amino acids (SEQ ID NO. 4).

EXAMPLE 2

Detection of PI3Kγ at a protein and transcript level

A polyclonal rabbit antiserum against PI3Kγ was produced by immunization with a 15 amino acid long peptide of the sequence NSQLPESFRVPYDPG SEQ ID NO:5 (corresponding to amino acids 741 to 755 in SEQ ID NO. 2 or amino acids 742 to 756 in SEQ ID NO. 4). The serum was purified by protein A chromatography and affinity chromatography using the peptide antigen coupled to Actigel (Sterogene).

Figure 1:
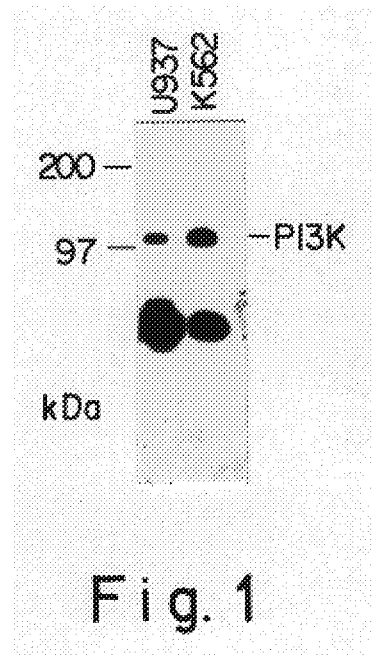
FIG. 1 shows the detection of PI3Kγ in human blood cells by specific antibodies.

PI3Kγ can be detected as a 110 kDa protein using this antiserum by immunoprecipitation and Western blot analysis of U937 and K562 cells (FIG. 1). The immunoprecipitation and Western blot were carried out according to the method of Hiles et al. (Cell 70 (1992) 419–429). A conjugate of horseradish peroxidase and anti-rabbit antiserum (Sigma, 1:2000 dilution) was used as the secondary antibody. The bound peroxidase was visualized by chemiluminescence.

A Northern blot analysis of human tissue from the pancreas, kidney, skeletal muscle, liver, lung, placenta, brain and heart each showed different concentrations of a 5.3 kb long mRNA.

EXAMPLE 3

Recombinant expression of PI3Kγ

Figure 2A:
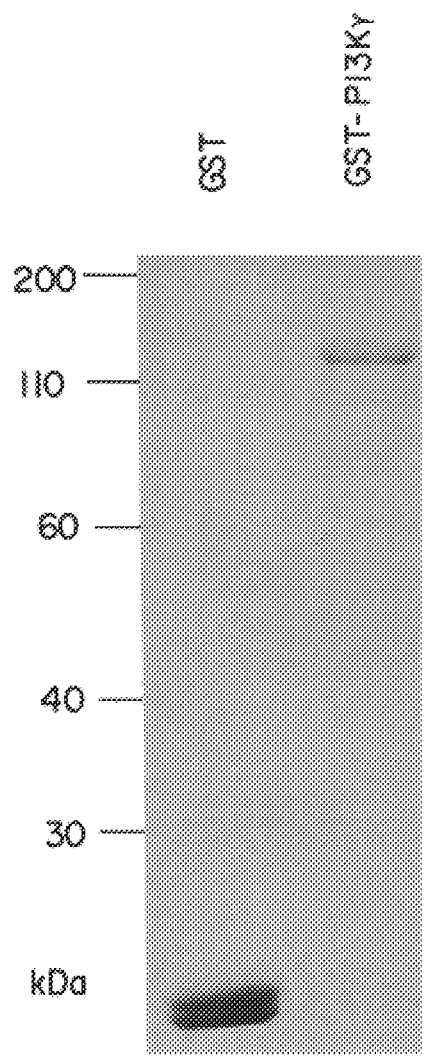
FIG. 2a shows the recombinant expression of PI3Kγ in insect cells.

The DNA coding for PI3Kγ was cloned into the vector pAcG2T (Davis et al., Biotechnology 11 (1993), 933–936). The resulting recombinant vector pAcG2T-PI3Kγ contained the PI3Kγ cDNA from codon 4 onwards in a fusion with the glutathione S transferase (GST) gene. Sf9 cells were cotransfected with pAcG2T-PI3Kγ and linearized baculovirus DNA (BaculoGold, Pharmingen). Individual recombinant baculovirus GST-PI3Kγ plaques were purified and amplified. The expression and purification of recombinant protein were carried out using standard protocols (Dhand et al., EMBO J. 13 (1994), 511–521). FIG. 2a shows the expression of recombinant PI3Kγ GST fusion protein or GST alone after fractionation on a SDS polyacrylamide gel. The detection was carried out by staining with coomassie blue.

Figure 2B:
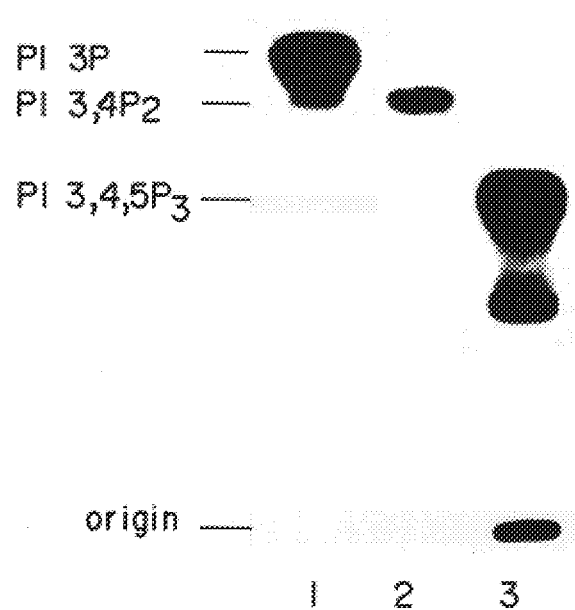
FIG. 2b shows the detection of the enzymatic activity of purified recombinant PI3Kγ.

FIG. 2b shows a detection of the enzymatic activity of purified recombinant PI3Kγ. Phosphatidylinositol (PI, lane 1), phosphatidylinositol-4-phosphate (PI4-P, lane 2) and phosphatidylinositol-4,5-diphosphate (PI 4,5-P$_2$, lane 3) were used as substrates. The test was carried out essentially according to the method of Stephens et al. (Cell 77 (1994), 83–93) but without cholate. 30 μl sonicated lipid vesicles containing 320 μM phosphatidyl ethanolamine, 140 μM phosphatidyl choline, 300 μM phosphatidyl serine, 30 μM sphingomyelin and 320 μM substrate were added to 10 μl enzyme (0.1 ng) and incubated for 8 minutes on ice. The test was started by addition of 10 μl 20 μM ATP containing 10 μCi γ($^{32}$P)ATP and incubated for 15 minutes at room temperature. The extracted lipids were separated and visualized. The identity of the 3-phosphorylated phosphoinositides was confirmed by anion exchange HPLC after deacylation of the lipids (Auger et al., Cell 57 (1989), 167–175).

FIG. 2b shows that the substrates were phosphorylated in the D-3 position of the inositol ring. In addition it was found that PI3Kγ was inhibited by wortmannin at nanomolar concentrations.

EXAMPLE 4

Regulation of PI3Kγ

In order to detect an interaction between the regulatory and adaptory subunits of p85 (p85α and p85β) and PI3Kγ, human PI3Kγ and bovine PI3Kα (Hiles et al., supra) were expressed in Sf9 insect cells according to the process described in example 3 as GST fusion proteins either alone or together with p85α and p85β. After lysis and centrifugation of the cells, glutathione-Sepharose was added to the supernatant in order to bind the GST fusion proteins. The particles were washed and analysed by SDS-PAGE and Western-blot. PI3Kγ was detected using the polyclonal antipeptide antibody described in example 2. Appropriate mixtures of specific monoclonal antibodies (Dhand et al., supra) as a primary antibody and conjugates of horseradish peroxidase and anti-mouse antibodies (Dianova, 1:4000 dilution) as the secondary antibody were used to detect p85α, p85β and bovine PI3Kα.

Figure 3:
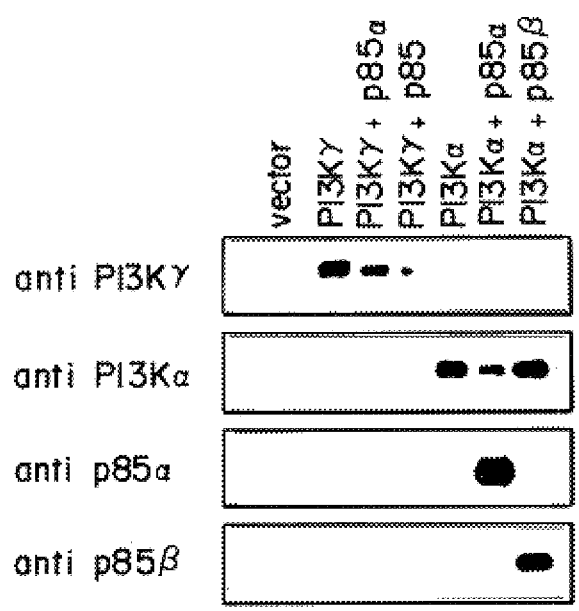
FIG. 3 shows the absence of interaction between PI3Kγ and the proteins p85α and p85β.

FIG. 3 shows that PI3Kγ in contrast to PI3Kα does not bind to p85α and p85β subunits. The regulation mechanism of PI3Kγ is therefore different from PI3Kα.

In order to detect an interaction between PI3Kγ and G proteins, purified recombinant human PI3Kγ and bovine PI3Kα was incubated with the transducin species G$_t$βγ. A substantial amplification of the kinase activity of PI3Kγ was found. This stimulation was suppressed by adding GTP-loaded G$_t$α which confirms the specificity of the interaction.

In contrast the enzymatic activity of PI3Kα could not be stimulated by addition of G$_t$βγ. A similar activation of the enzyme was found after addition of Gα in the presence of 20 μM AlCl$_3$ and 10 mM NaF. The complex Gα-GDP-AlF$_4^-$ acts as an activating species.

The determination of activity was carried out as described in example 3. The G$_t$ proteins purified from bovine retina according to the method of Camps et al. (Nature 360 (1992) 684–686) were incubated on ice with the lipid vesicles for 5 min (G$_t$βγ) or for 20 min (G$_t$βγ plus G$_t$α-GTP) before adding the enzyme.

Binding studies with recombinant PI3Kγ showed that the regulator protein Ras in its active GTP-loaded form associates with the enzyme. Ras in its constitutively active version is able to oncogenically transform cells. Hence this is a further indication for the potential importance of PI3Kγ in the regulation of cellular proliferation.

We claim:

1. An isolated nucleic acid comprising:

(a) a nucleotide sequence encoding an active phosphatidylinositol-3-kinase consisting of the amino acid sequence set forth in SEQ ID NO:2;

(b) a nucleotide sequence encoding an active phosphatidylinositol-3-kinase consisting of the amino acid sequence set forth in SEQ ID NO:4; or (c) a nucleotide sequence which hybridizes with the nucleotide sequence of (a) or (b) after washing at 55° C. in an aqueous low salt buffer containing 0.2×SSC or 0.1% SDS.

2. The nucleic acid of claim 1, wherein the nucleic acid is a recombinant DNA molecule.

3. The nucleic acid of claim 1, wherein the nucleic acid comprises a nucleotide sequence consisting of:

(a) the protein-coding sequence set forth in nucleotides 423–3569 of SEQ ID NO: 1;

(b) the protein-coding sequence set forth in nucleotides 423–3572 of SEQ ID NO: 3; or (c) a sequence which hybridizes with the protein-coding sequence of (a) or (b) after washing at 55° C. in an aqueous low salt buffer containing 0.2×SSC or 0.1% SDS.

4. The nucleic acid of claim 1, wherein the nucleic acid comprises a nucleotide sequence which hybridizes with the protein-coding sequence of (a) or (b) after washing at 62° C. in an aqueous low salt buffer containing 0.2×SSC or 0.1% SDS.

5. The nucleic acid of claim 1, wherein the nucleic acid comprises a nucleotide sequence which hybridizes with the protein-coding sequence of (a) or (b) after washing at 68° C. in an aqueous low salt buffer containing 0.2×SSC or 0.1% SDS.

6. An isolated nucleic acid comprising a nucleotide sequence of at least 20 consecutive nucleotides of the nucleotide sequence of SEQ ID NO:1 or SEQ ID NO:3, wherein the nucleotide sequence is specific for nucleic acid encoding phosphatidylinositol-3-kinase γ.

7. A vector, comprising the nucleic acid of one of claims 1–6.

8. A transformed cell, containing the nucleic acid of one of the claims 1–6.

9. A transformed cell, containing the vector of claim 7.

10. A method for determining a phosphatidylinositol-3-kinase mRNA produced in cells, comprising incubating a nucleic acid probe comprising a phosphatidylinositol-3-kinase-mRNA-specific region of the nucleic acid of claim 1 with the phosphatidylinositol-3-kinase mRNA and determining any binding between the probe and the mRNA.

11. The method of claim 10, wherein the cells are human cells.

* * * * *